US011898166B2

(12) United States Patent
Vizcardo et al.

(10) Patent No.: US 11,898,166 B2
(45) Date of Patent: Feb. 13, 2024

(54) IN VITRO GENERATION OF THYMIC ORGANOID FROM HUMAN PLURIPOTENT STEM CELLS

(71) Applicant: The United States of America, as represented by the Secretary, Department of Health and Human Services, Bethesda, MD (US)

(72) Inventors: Raul E. Vizcardo, Foster City, CA (US); Nicholas P. Restifo, Chevy Chase, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 470 days.

(21) Appl. No.: 16/648,008

(22) PCT Filed: Sep. 19, 2018

(86) PCT No.: PCT/US2018/051625
§ 371 (c)(1),
(2) Date: Mar. 17, 2020

(87) PCT Pub. No.: WO2019/060336
PCT Pub. Date: Mar. 28, 2019

(65) Prior Publication Data
US 2020/0270571 A1 Aug. 27, 2020

Related U.S. Application Data

(60) Provisional application No. 62/560,908, filed on Sep. 20, 2017.

(51) Int. Cl.
*C12N 5/078* (2010.01)
*A61K 35/26* (2015.01)

(52) U.S. Cl.
CPC ............. *C12N 5/065* (2013.01); *A61K 35/26* (2013.01); *C12N 2500/98* (2013.01); *C12N 2501/105* (2013.01); *C12N 2501/117* (2013.01); *C12N 2501/15* (2013.01); *C12N 2501/41* (2013.01); *C12N 2501/415* (2013.01); *C12N 2506/45* (2013.01); *C12N 2513/00* (2013.01)

(58) Field of Classification Search
CPC ............. C12N 5/065; C12N 2500/98; C12N 2501/105; C12N 2501/117; C12N 2501/15; C12N 2501/41; C12N 2501/415; C12N 2506/45; C12N 2513/00; A61K 35/26
See application file for complete search history.

(56) References Cited

U.S. PATENT DOCUMENTS

| 8,034,334 B2 | 10/2011 | Dudley et al. |
| 8,383,099 B2 | 2/2013 | Dudley et al. |
| 2010/0178700 A1 | 7/2010 | Fletcher et al. |
| 2012/0244133 A1 | 9/2012 | Rosenberg et al. |
| 2015/0284689 A1 | 10/2015 | Nigam |

FOREIGN PATENT DOCUMENTS

| WO | WO 2010/143529 A1 | 12/2010 |
| WO | WO 2014/066649 A1 | 5/2014 |
| WO | WO 2017075389 A1 | 5/2017 |

OTHER PUBLICATIONS

Inami et al., Differentiation of induced pluripotent stem cells to thymic epithelial cells by phenotype, Immunology and Cell Biology, 89: 314-321. (Year: 2011).*
Benton et al., Advancing science and technology via 3D culture on basement membrane matrix, Journal of Cellular Physiology, p. 18-25. (Year: 2009).*
Chase et al., Development and characterization of a clinically compliant xeno-free culture medium in good manufacturing practice for human multipotent mesenchymal stem cells, Stem Cells Translational Medicine, 1: 750-758. (Year: 2012).*
Kieper et al., Overexpression of interleukin (IL)-7 to IL-15-independent generation of memory phenotype CD8+ T cells, Journal of Experimental Medicine, 195(12): 1533-1539. (Year: 2002).*
Truong et al., In situ-forming click-crosslinked gelatin based hydrogels for 3D culture of thymic epithelial cells, Biomaterials Sciences, 4: 1123-1131. (Year: 2016).*
Hun et al., Native thymic extracellular matrix improves in vivo thymic organoid T cell output, and drives in vitro thymic epithelial cell differentiation, Biomaterials, 118: 1-15. (Year: 2017).*
Vizcardo et al., "Generation fo Tumor Antigen-Specific iPSC-Derived Thymic Emigrants Using a 3D Thymic Culture System", *Cell Reports*, vol. 22, Issue 12, pp. 3175-3190 (2018).
Vizcardo et al., "A Three-dimensional Thymic Culture System to Generate Murine Induced Pluripotent Stem Cell-derived Tumor Antigen-specific Thymic Emigrants", *Journal of Visualized Experiments*, vol. 150, e58672, doi:10.3791/58672 (2021).
Boyd et al., "Rewiring Immunity: Generating a Functional Thymus from hESCs . . . Are We There Yet?" *Cell Stem Cell*, 13:135-136 (Aug. 1, 2013).
Fan et al., "Bioengineering Thymus Organoids to Restore Thymic Function and Induce Donor-Specific Immune Tolerance to Allografts," *Molecular Therapy*, 23(7): 1262-1277 (Jul. 2015).
Gattinoni et al., "Acquisition of Full Effector Function in Vitro Paradoxically Impairs the in Vivo Antitumor Efficacy of Adoptively Transferred CD8+ T Cells," *Journal of Clinical Investigation*, 115(6): 1616-1626 (Jun. 2005).

(Continued)

*Primary Examiner* — Laura Schuberg
*Assistant Examiner* — Joseph Paul Miano
(74) *Attorney, Agent, or Firm* — Leydig, Voit & Mayer, Ltd.

(57) ABSTRACT

Disclosed are methods of preparing thymic organoids according to embodiments of the invention. Also disclosed are methods of preparing thymic emigrant cells in vitro, according to embodiments of the invention. Also disclosed are methods of treating or preventing a condition in a mammal, e g., cancer.

13 Claims, 23 Drawing Sheets

(56) References Cited

OTHER PUBLICATIONS

Ohigashi, et al., "Development and Developmental potential of cortical thymic epithelial cells," *Immunological Reviews*, 271(1):10-22 (May 2016).

Parent et al., "Generation of Functional Thymic Epithelium from Human Embryonic Stem Cell that Supports Host T Cell Development," *Cell Stem Cell*, 13(2): 1-18 (Dec. 20, 2013) Author Manuscript.

Rosenberg et al. "Durable Complete Responses in Heavily Pre-treated Patients with Metastatic Melanoma Using T-Cell Transfer Immunotherapy," *Clin Cancer Res* 17(13): 4550-4557 (Jul. 1, 2011).

Seet, et al., "Artificial Thymic Organoid Cultures: In vitro Human T-cell Differentiation from Hematopoietic Stem and Progenitor Cells," Nature, www.nature.comprotocolexchange/protocols/5725; 2017; 14 pgs.

Seet et al., "Generation of Mature T Cells from Human Hematopoietic Stem and Progenitor Cells in Artificial Thymic Organoids," *Nature Methods*, 14(5): 521-529 (May 2017).

Soh et al., "FOXN1GFP/w Reporter hESCs Enable Identification of Intergrin-ß4, HLA-DR, and EpCAM as Markers of Human PSC-Derived FOXN1+ Thymic Epithelial," *Stem Cell Reports*, 2: 925-937 (Jun. 3, 2014).

Sun et al., "Directed Differentiation of Human Embryonic Stem Cells into Thymic Epithelial Progenitor-like Cells Reconstitutes the Thymic Mircoenvironment in Vivo," *Cell Stem Cell*, 13(2): 230-236 (Aug. 1, 2013).

Takebe et al., "Vascularized and Functional Human Liver from an iPSC-derived Organ Bud Transplant," *Nature*, 499(7459): 481-484 (Jul. 25, 2013).

European Patent Office, International Search Report in International Application No. PCT/US2018/051625, dated Nov. 20, 2018.

European Patent Office, Written Opinion in International Application No. PCT/US2018/051625, dated Nov. 20, 2018.

International Bureau of WIPO, International Preliminary Report on Patentability in International Application No. PCT/US2018/051625, dated Apr. 2, 2020.

* cited by examiner

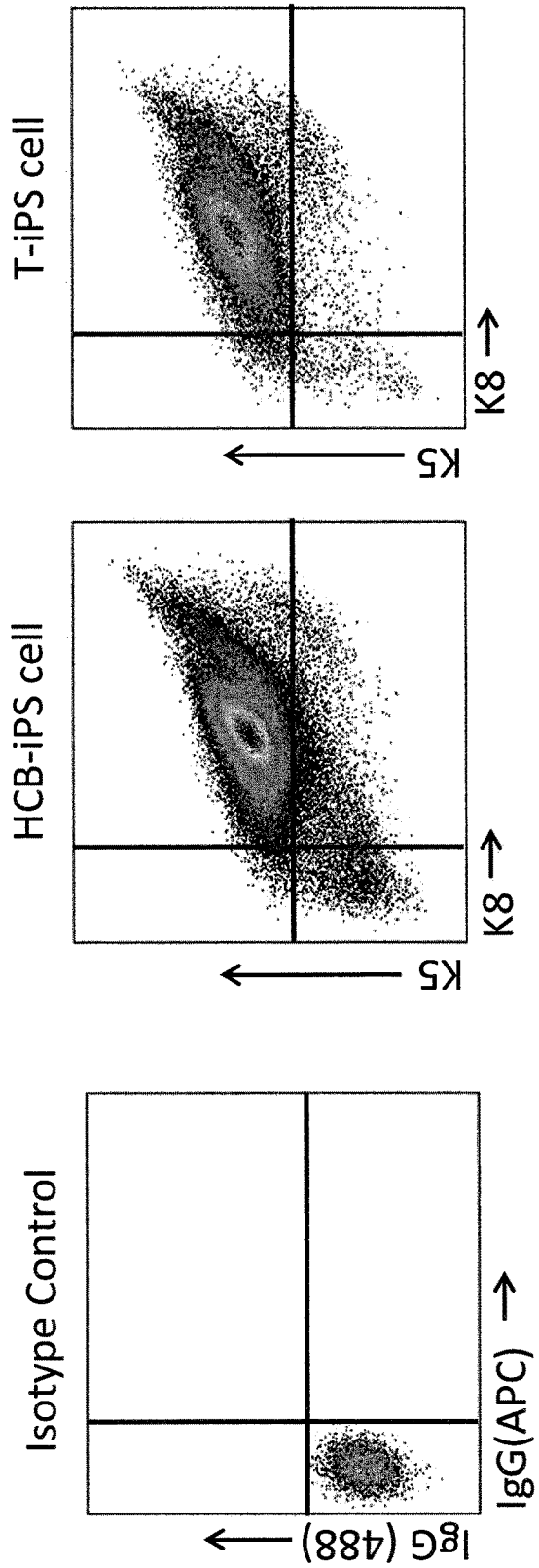
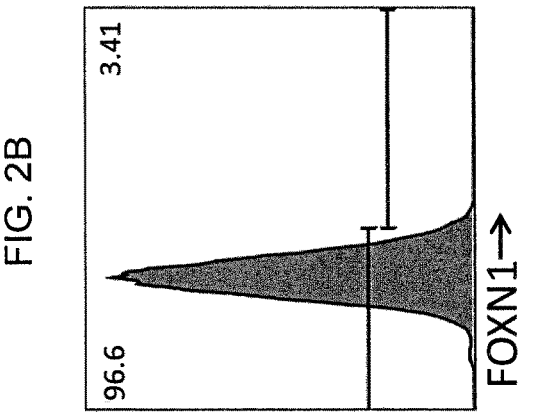
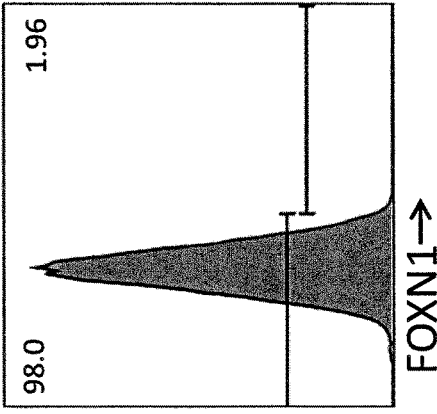
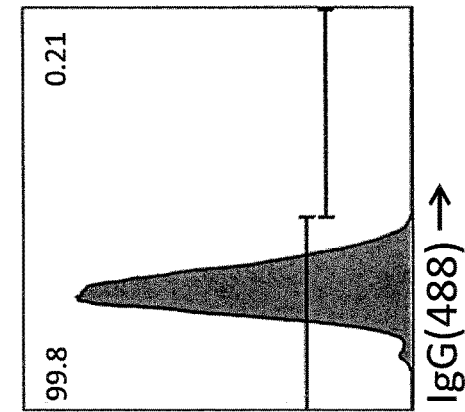
FIG. 2A  FIG. 2B  FIG. 2C
FIG. 2D  FIG. 2E  FIG. 2F

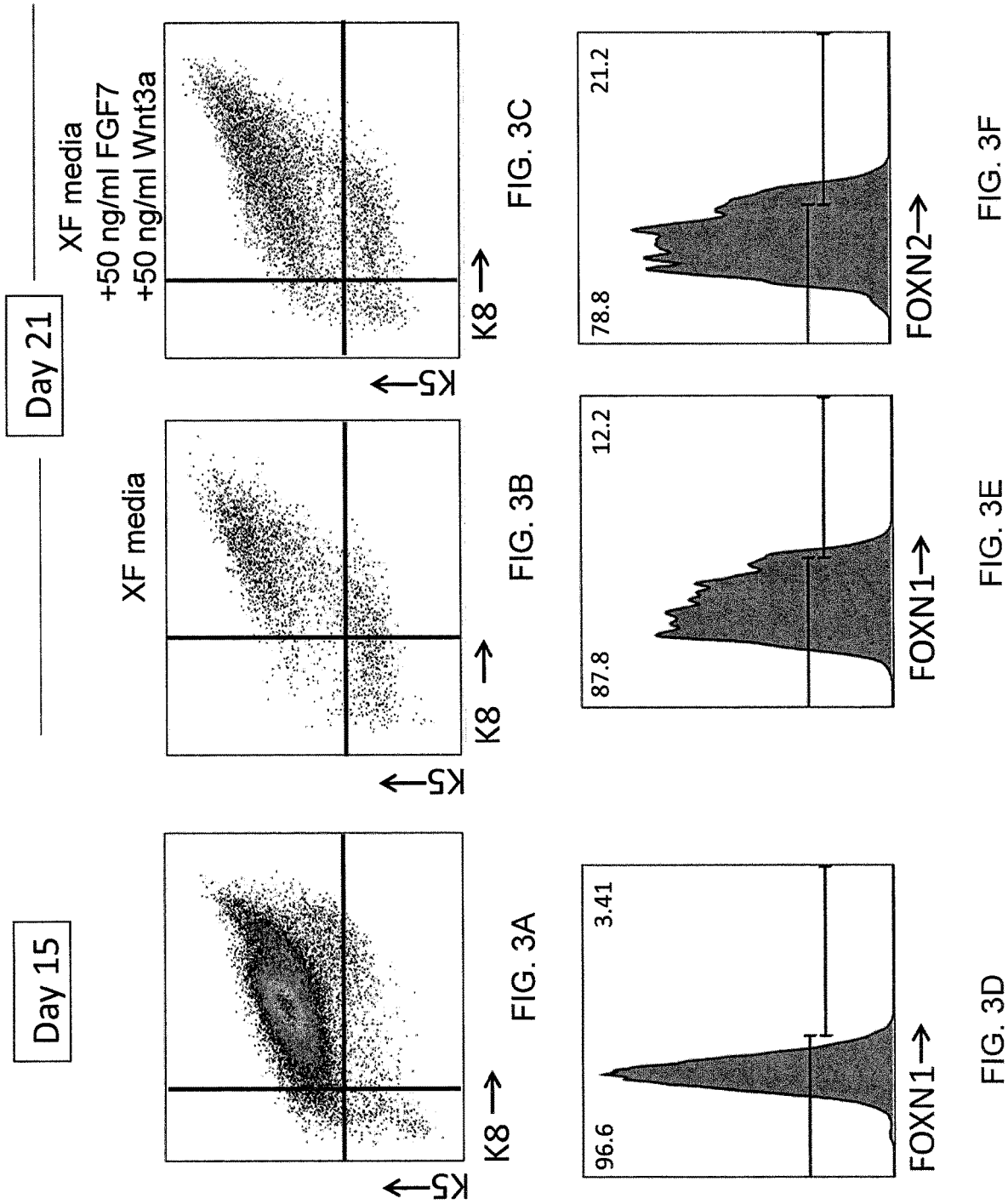

 Day 0: human iPS
 Day 5-9: Primitive Endoderm
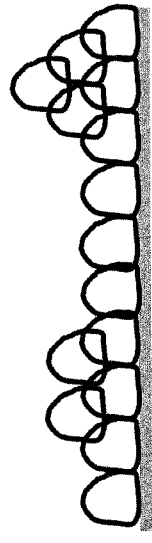 Day 9-13: Third Pharingeal Pouch
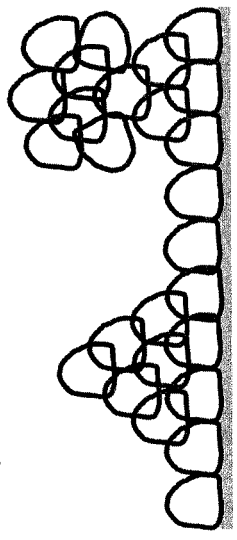 Day 14: Thymic Epithelial Progenitor-like cells
FIG. 4

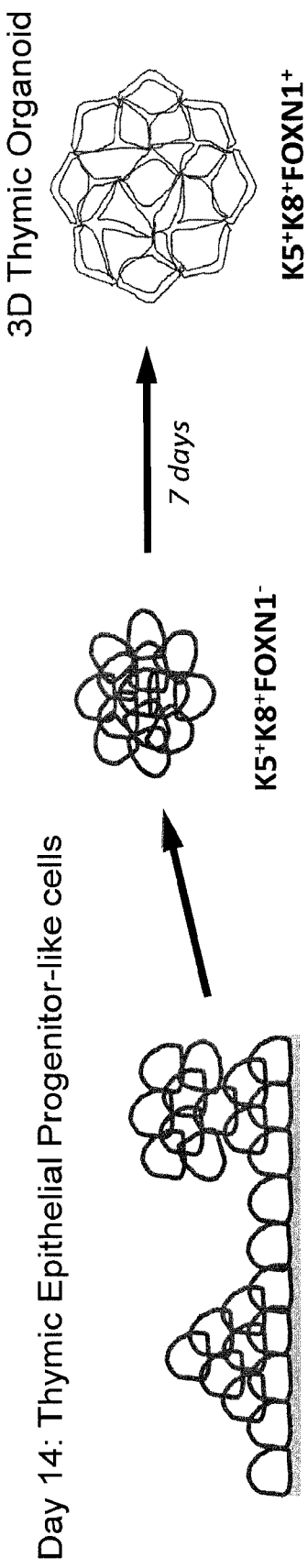
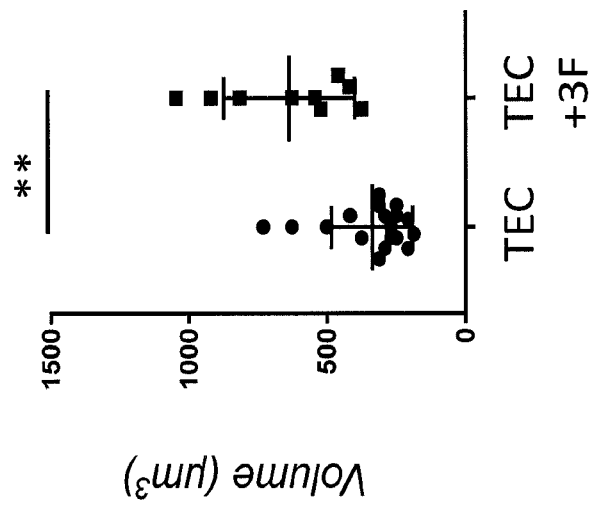
FIG. 5A
FIG. 5B

US 11,898,166 B2

IN VITRO GENERATION OF THYMIC ORGANOID FROM HUMAN PLURIPOTENT STEM CELLS

CROSS-REFERENCE TO RELATED APPLICATION APPLICATIONS

This patent application is the U.S. National Stage of PCT/US2018/051625, filed Sep. 19, 2018, which claims the benefit of U.S. Provisional Patent Application No. 62/560,908, filed Sep. 20, 2017, each of which is incorporated by reference in its entirety herein.

STATEMENT REGARDING FEDERALLY SPONSORED RESEARCH OR DEVELOPMENT

This invention was made with Government support under project number Z01BC010763 by the National Institutes of Health, National Cancer Institute, Surgery Branch. The Government has certain rights in the invention.

BACKGROUND OF THE INVENTION

Adoptive cell therapy (ACT) using cells of the T cell lineage may produce positive clinical results in the treatment of a variety of conditions, e.g., cancer. However, the production of cells of the T cell lineage in vitro or ex vivo may be challenging. Accordingly, there exists a need for improved materials and methods useful for preparing cells for ACT.

BRIEF SUMMARY OF THE INVENTION

An embodiment of the invention provides a method of preparing a thymic organoid in vitro, the method comprising: (i) differentiating pluripotent stem cells into endodermal cells in vitro; (ii) differentiating the endodermal cells into third pharyngeal pouch endodermal (PPE) cells in vitro; (iii) differentiating the third PPE cells into thymic epithelial progenitor-like cells (TEPLCs) in vitro; (iv) differentiating the TEPLCs into thymic epithelial progenitor cells (TEPCs) in an in vitro, three-dimensional culture; (v) differentiating the TEPCs into thymic epithelial cells (TECs) in the in vitro, three-dimensional culture in the presence of bone morphogenetic protein 4 (BMP4); and (vi) forming the TECs into a thymic organoid in the in vitro, three-dimensional culture, wherein the thymic organoid expresses any one or more of β5t, DLL4, and interleukin 7, and wherein the method does not comprise co-culturing the cells with mesenchyme or stromal cells.

Further embodiments of the invention provide a thymic organoid prepared by the inventive method.

Another embodiment of the invention provides a method of preparing thymic emigrant cells in vitro, the method comprising: migrating progenitor cells into the inventive thymic organoid, egressing the cells from the thymic organoid, wherein the cells egressing from the thymic organoid are thymic emigrant cells; and isolating the thymic emigrant cells from the thymic organoid.

Another embodiment of the invention provides a method of treating or preventing a condition in a mammal, the method comprising: preparing the thymic emigrant cells in vitro by the inventive method; and administering the thymic emigrant cells to the mammal in an amount effective to treat or prevent the condition in the mammal.

BRIEF DESCRIPTION OF THE SEVERAL VIEWS OF THE DRAWING(S)

FIG. 2A depicts experimental data illustrating the detection of isotype controls IgG (488) and IgG stained with allophycocyanin (APC) by flow cytometry.

FIG. 2B depicts experimental data illustrating the expression of K5 and K8 by CD34+ human cord blood cell (HCB)-derived induced pluripotent stem cells (iPS).

FIG. 2C depicts experimental data illustrating the expression of K5 and K8 by T cell derived iPS (T-iPS).

FIG. 2D depicts experimental data illustrating the detection of isotype control IgG (488) by flow cytometry. The number on the upper left corner of the histogram is the percentage of cells not detected using isotype control IgG (488). The number on the upper right corner represents the percentage of cells detected using isotype control IgG (488).

FIG. 2E depicts experimental data illustrating FOXN1 expression by CD34+ HCB-iPS cells. The number on the upper left corner of the histogram is the percentage of cells not expressing FOXN1. The number on the upper right corner represents the percentage of cells expressing FOXN1.

FIG. 2F depicts experimental data illustrating FOXN1 expression by T-iPS cells. The number on the upper left corner of the histogram is the percentage of cells not expressing FOXN1. The number on the upper right corner represents the percentage of cells expressing FOXN1.

FIG. 3A depicts experimental data illustrating the cellular expression of K5 and K8 in the isotype control IgG (488) on Day 15.

FIG. 3B depicts experimental data illustrating the cellular expression of K5 and K8 by HCB-iPS cells in XF media on Day 21.

FIG. 3C depicts experimental data illustrating cellular expression of K5 and K8 by T-iPS cells in XF media on Day 21 with 50 ng/ml FGF7 and 50 mg/ml Wnt3a.

FIG. 3D depicts experimental data illustrating cellular expression of FOXN1 of the control cells on Day 15. The number on the upper left corner of the histogram is the percentage of cells not expressing FOXN1. The number on the upper right corner represents the percentage of cells that express FOXN1.

FIG. 3E depicts experimental data illustrating cellular expression of FOXN1 in XF media on Day 21. The number on the upper left corner of the histogram is the percentage of cells not expressing FOXN1. The number on the upper right corner represents the percentage of cells that express FOXN1.

FIG. 3F depicts experimental data illustrating cellular expression of FOXN1 on Day 21 in XF media with 50 ng/ml FGF7 and 50 mg/ml Wnt3a. The number on the upper left corner of the histogram is the percentage of cells not expressing FOXN1. The number on the upper right corner represents the percentage of cells that express FOXN1.

FIG. 4 is a schematic showing the differentiation of human iPS (Day 0) into primitive endoderm (Days 5-9), into third pharyngeal pouch (Days 9-13), and into thymic epithelial progenitor-like cells (Day 14), in accordance with an embodiment of the invention.

FIG. 5A is a schematic showing differentiation of TEPLCs into K5+K8+FOXN1-cell spheroids which, in turn, differentiate into a K5+K8+FOXN1+ thymic organoid in accordance with an embodiment of the invention.

FIG. 5B is a graph depicting the volume of TEC (μm3) grown in the presence or absence of 3 factors (3F): BMP4, Wnt3a, and FGF7 (KGF).

Figure 6:
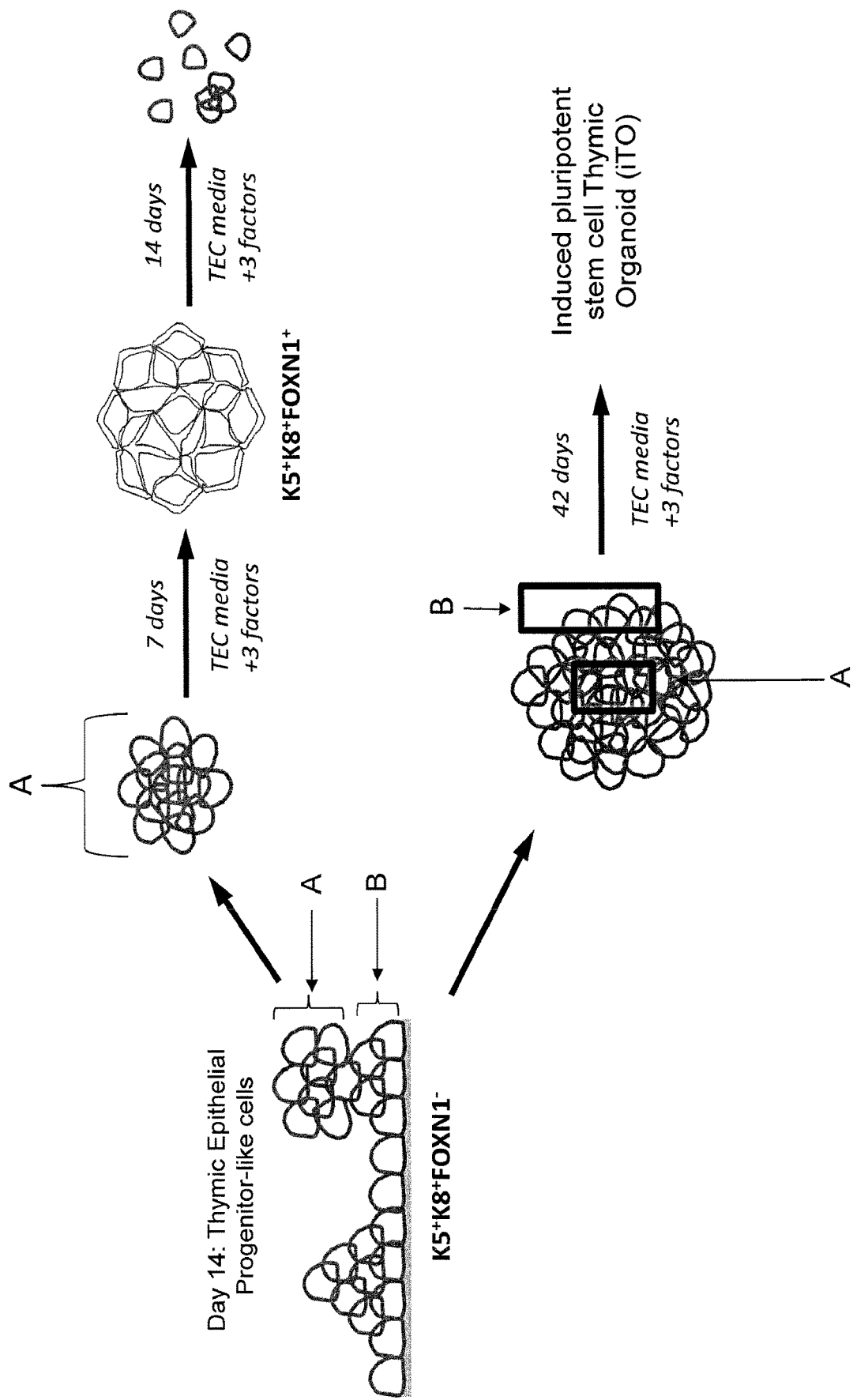

FIG. 6 is a schematic showing the differentiation of TEPLCs into a thymic organoid that ultimately disintegrates (top) compared to differentiation of TEPLCs into a viable induced pluripotent stem cell thymic organoid (iTO) (bottom) in accordance with embodiments of the invention. Cells designated as "A" indicate older, more differentiated cells. Cells designated as "B" indicate younger, less differentiated cells.

Figure 7:
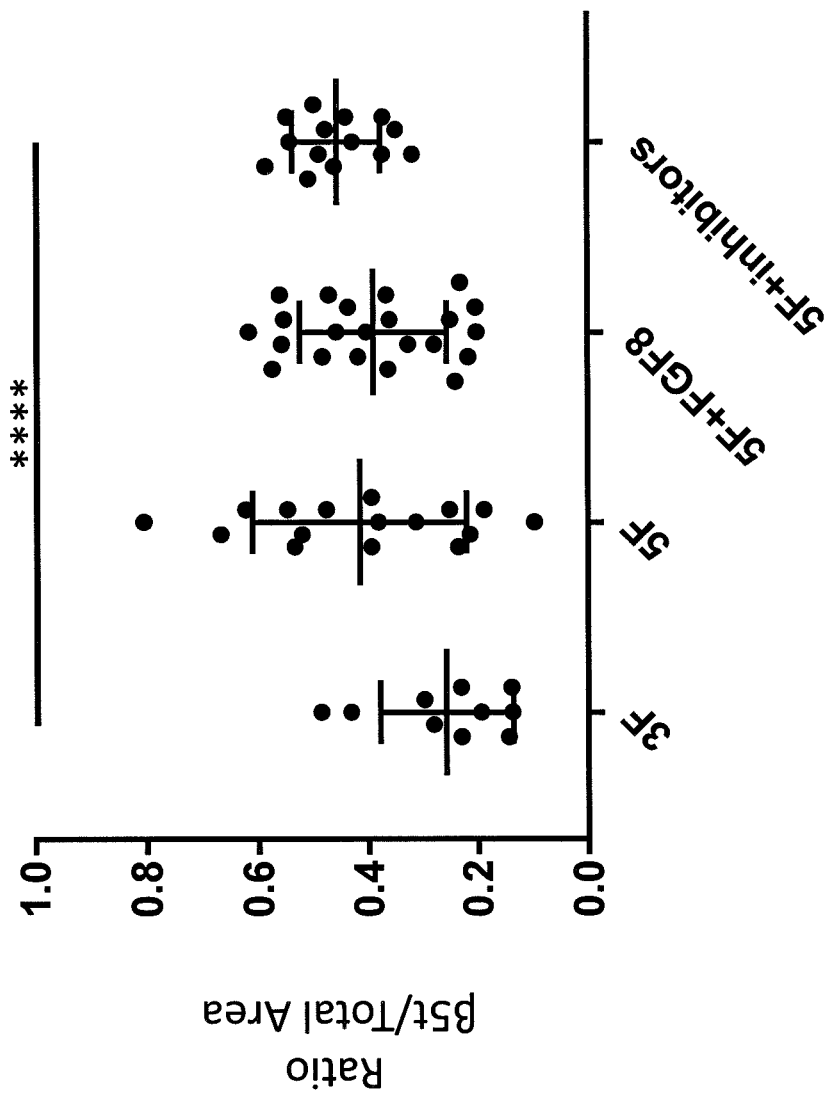

FIG. 7 is a graph which depicts experimental data illustrating the ratio of β5t expression compared with the total organoid area for organoids grown in different media. The Y-axis represents the ratio of β5t expression compared with the total organoid area. The X-axis represents the different culture media used to grow the organoids. The 3F media includes TEC expansion media+100 ng/ml Wnt3a+101 ng/ml FGF7+50 ng/ml BMP4. The 5F media includes TEC expansion media plus 100 mg/ml FGF8, 100 ng/ml FGF10, 100 ng/ml IGF-1, KAAD-Cyclopamine 0.5 μM and TGFP-RI Kinase inhibitor 5 μM (LY364947, Tocris, Bio-Techne Corporation, Minneapolis, MN). The 5F media+FGF8 includes the 5F media described above, with the addition of fibroblast growth factor 8. The 5F+inhibitors media includes the 5F media described above, with the addition of TGFP-RI Kinase inhibitor.

Figure 8:
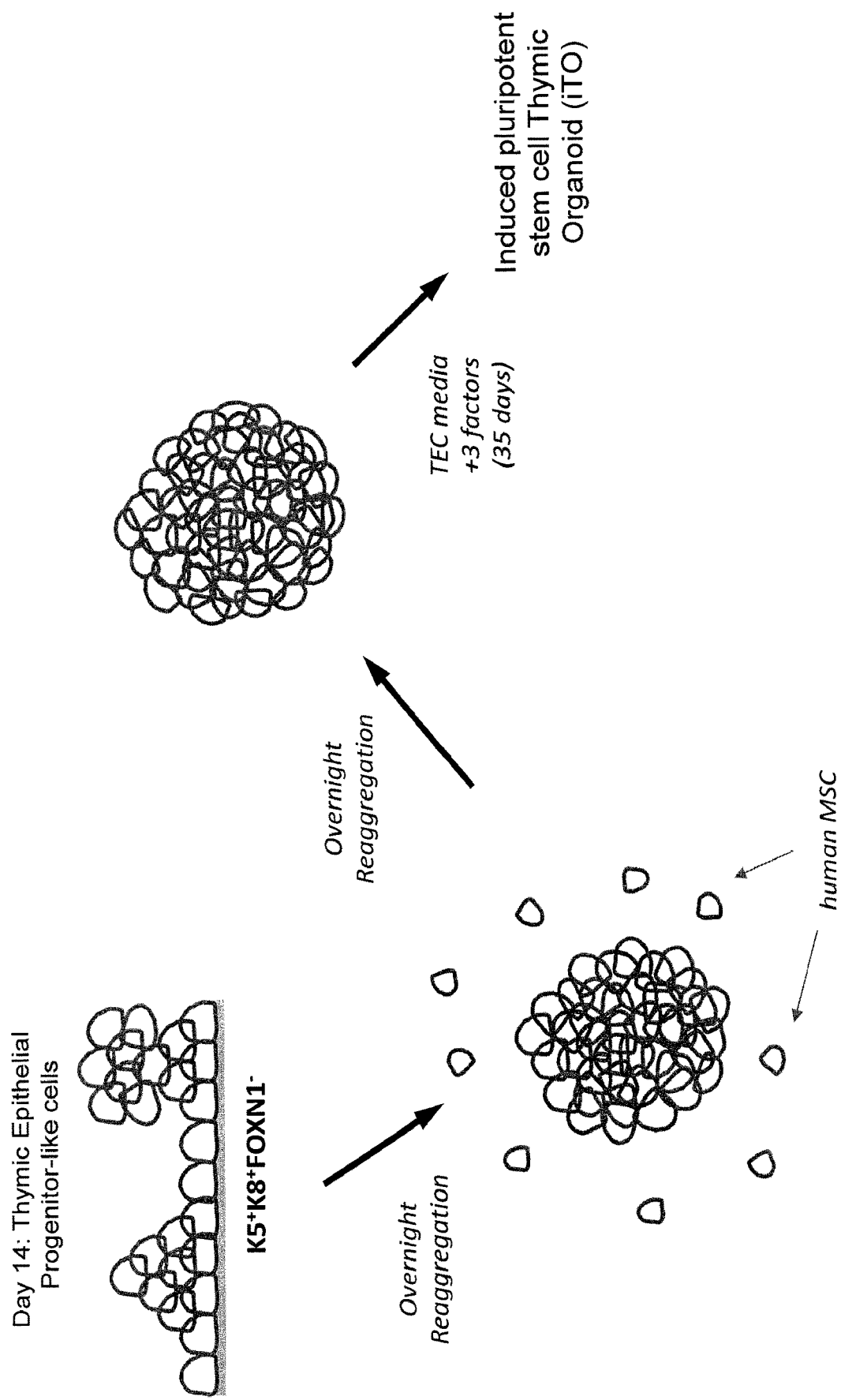

FIG. 8 is a schematic showing an experimental design protocol to test whether addition of human MSC factors can improve organoid formation in accordance with an embodiment of the invention.

Figure 9:
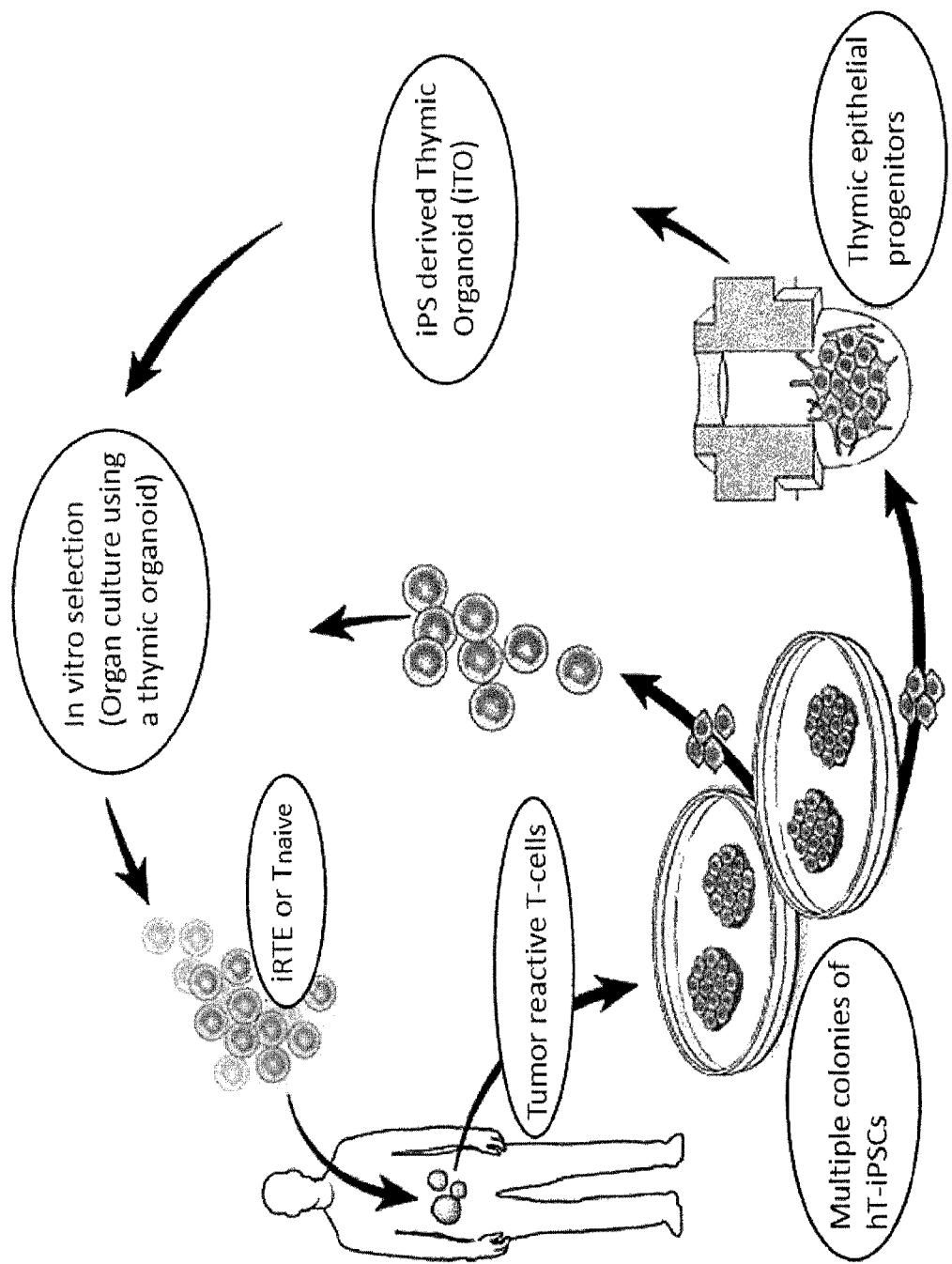

FIG. 9 is a schematic illustrating methods of treatment in accordance with embodiments of the invention.

Figure 10A:
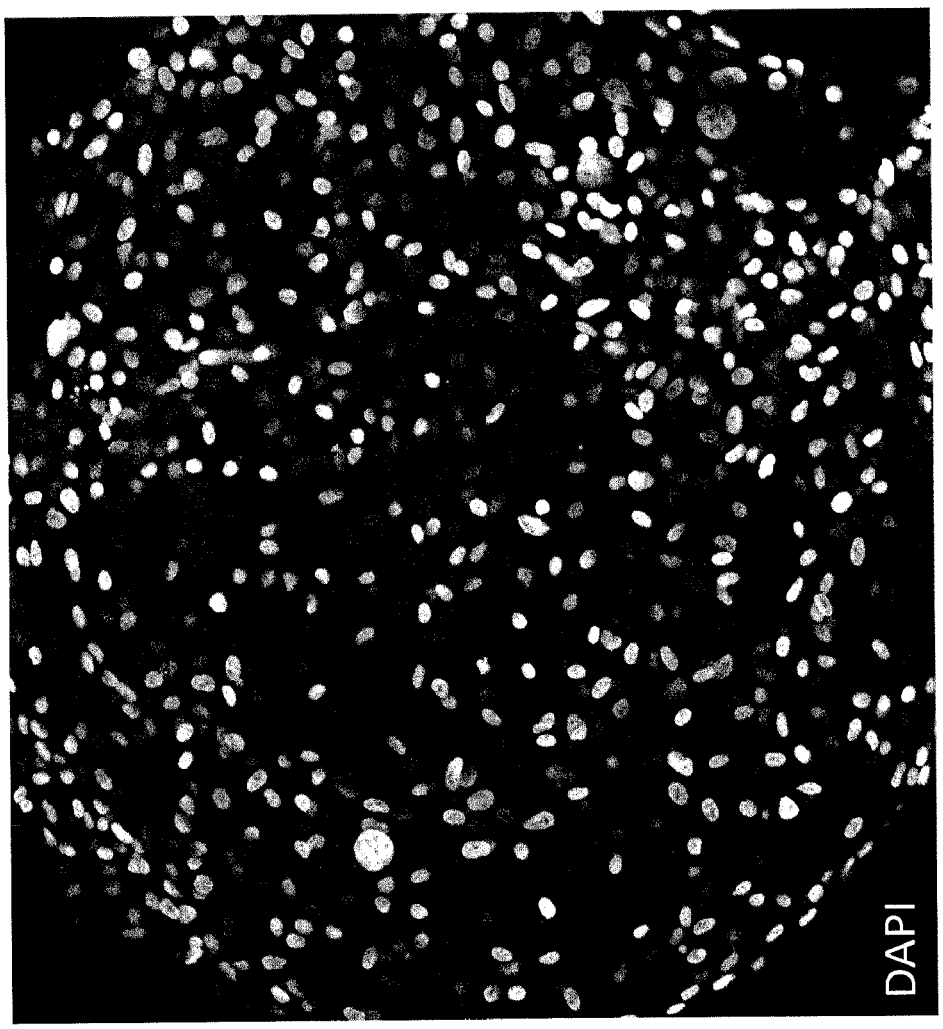

FIG. 10A is an image of an hiPSC-derived organoid taken via confocal microscope after 7 days of 3D culture, illustrating the detection of cell nuclei by DAPI staining.

Figure 10B:
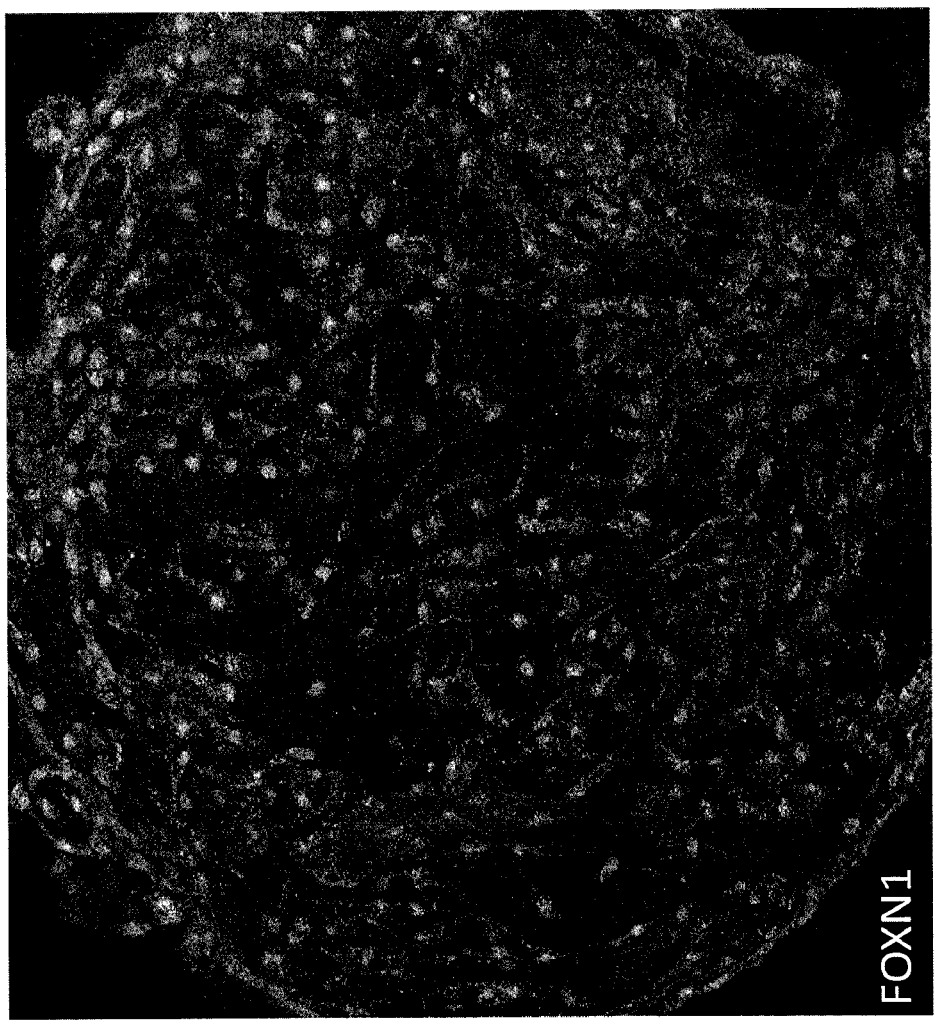

FIG. 10B is an image of the same hiPSC-derived organoid taken in FIG. 10A via confocal microscope after 7 days of 3D culture, illustrating the detection of anti-FOXN1 antibodies conjugated with ALEXA FLUOR secondary antibodies staining.

Figure 11A:
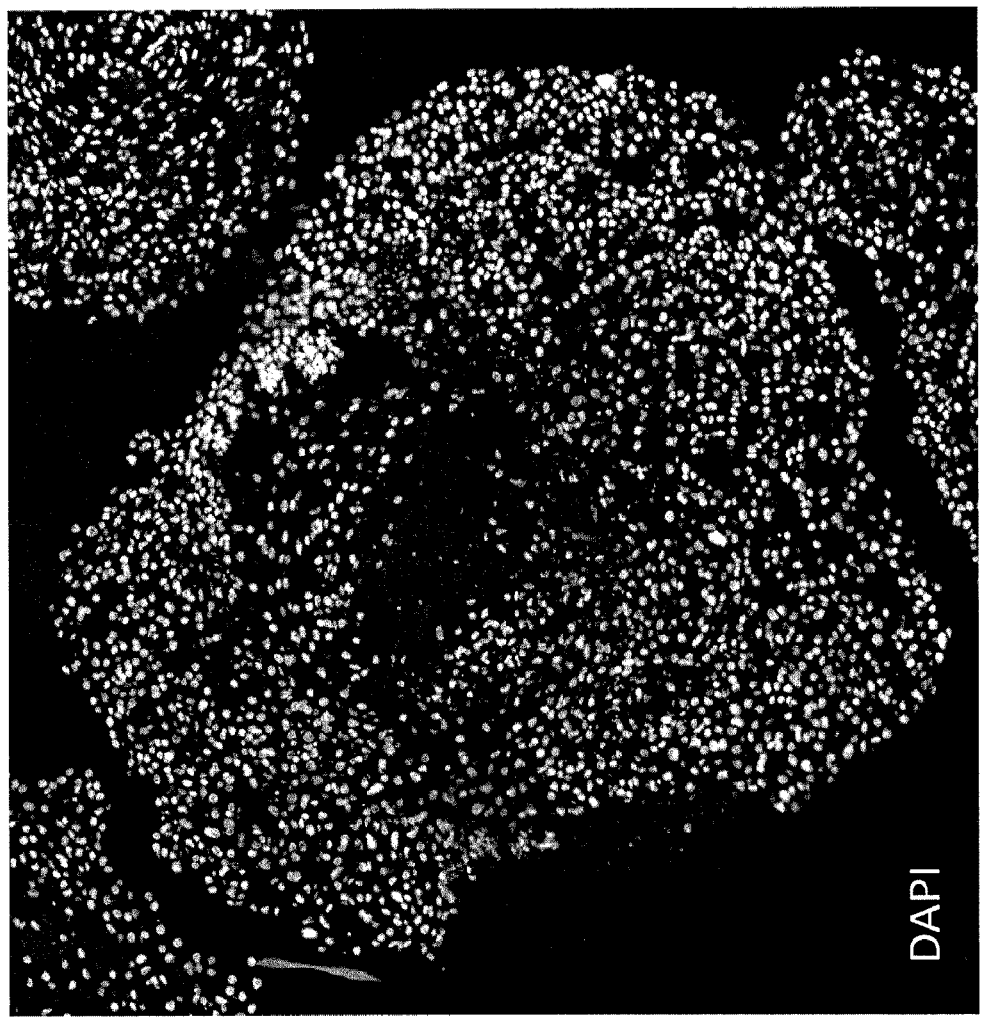

FIG. 11A is an image of an hiPSC-derived organoid taken via confocal microscope after 42 days of 3D culture, illustrating the detection of cell nuclei stained with DAPI.

Figure 11B:
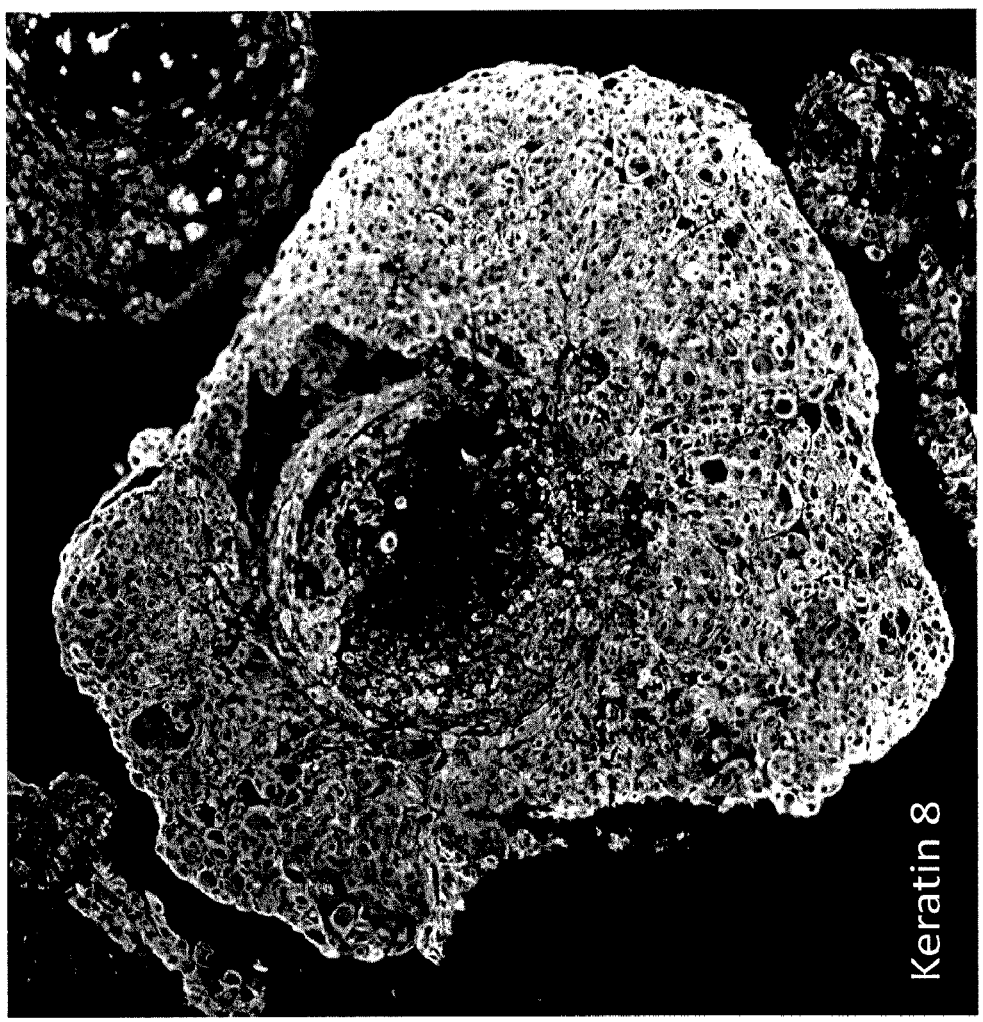

FIG. 11B is an image of the same hiPSC-derived organoid taken via confocal microscope shown in FIG. 11A, illustrating the detection of anti-Keratin-8 antibodies conjugated with ALEXA FLUOR secondary antibodies.

Figure 12A:
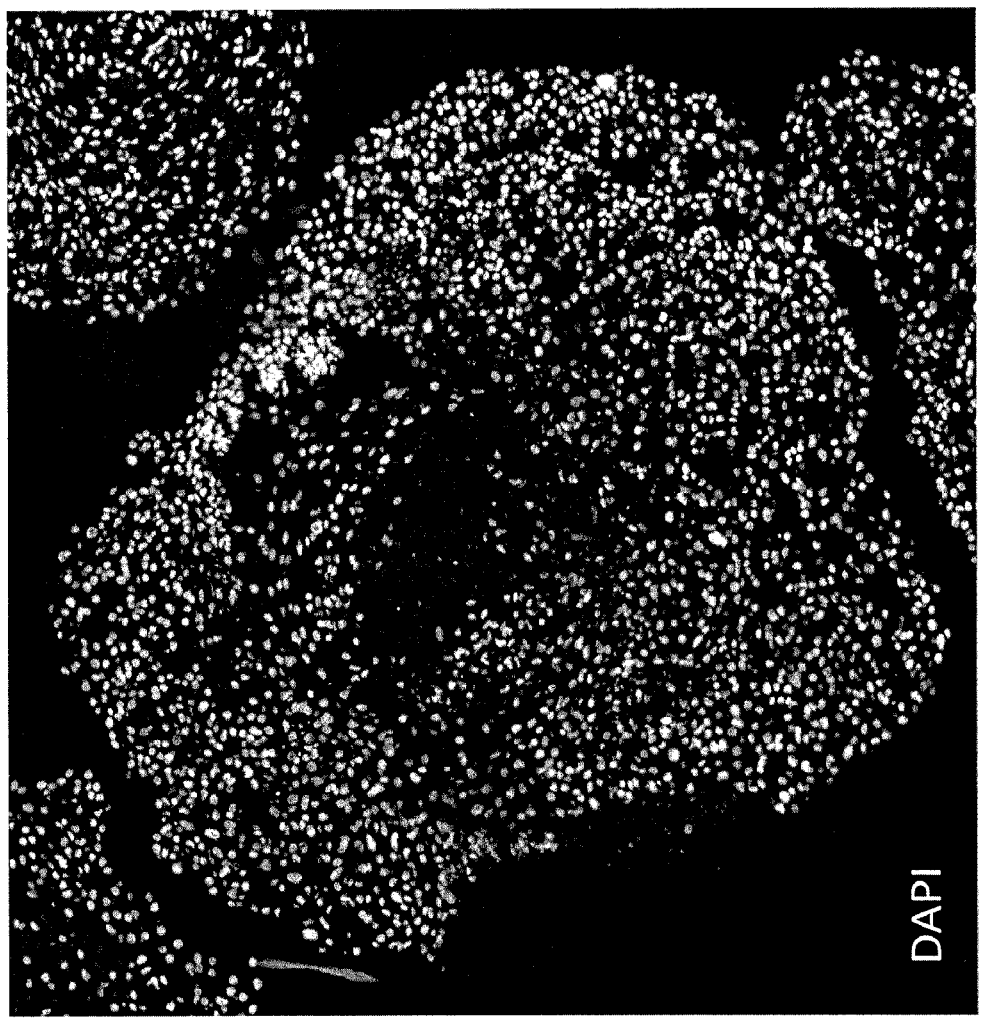

FIG. 12A is an image of the hiPSC-derived organoid taken via confocal microscope after 42 days of 3D culture shown in FIG. 11A, illustrating the detection of cell nuclei stained with DAPI.

Figure 12B:
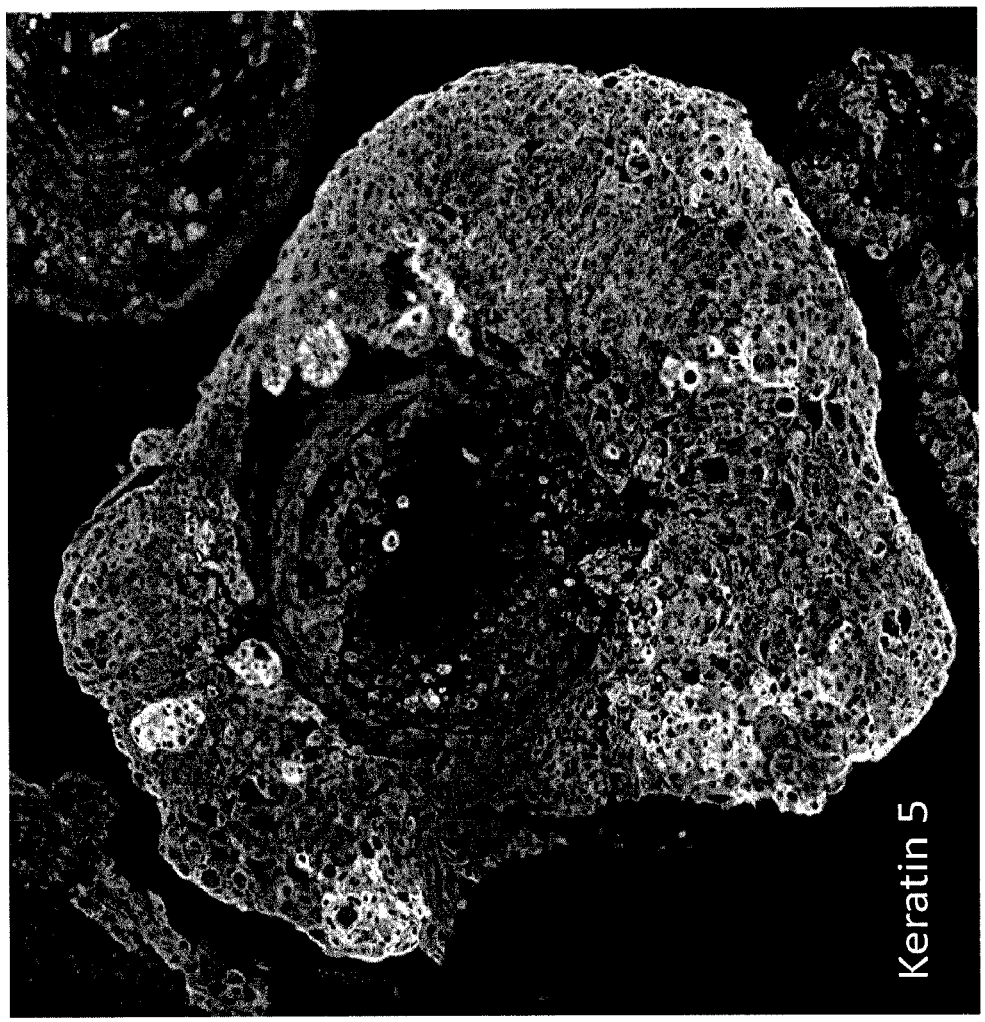

FIG. 12B is an image of the same hiPSC-derived organoid taken via confocal microscope shown in FIG. 12A, illustrating the detection of anti-Keratin-5 antibodies conjugated with ALEXA FLUOR secondary antibodies.

Figure 13A:
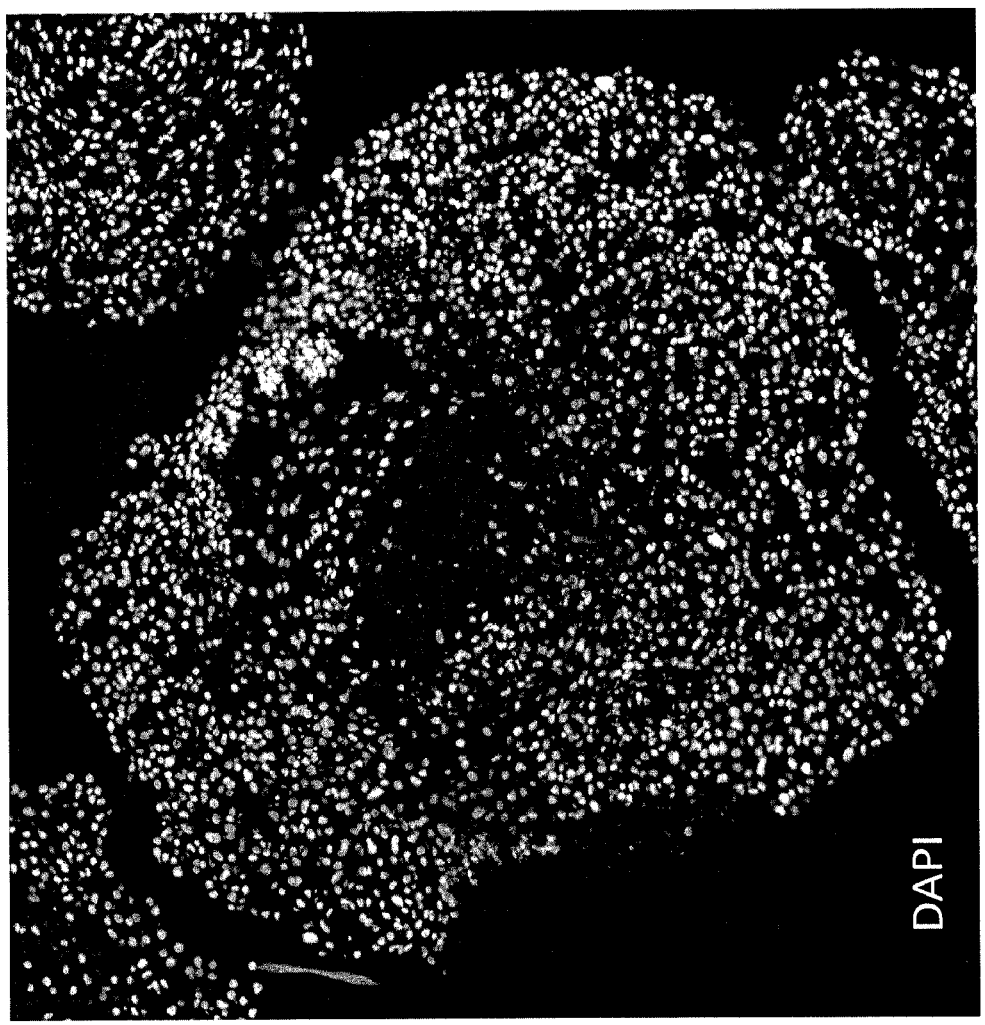

FIG. 13A is an image of the hiPSC-derived organoid taken via confocal microscope after 42 days of 3D culture shown in FIG. 11A, illustrating the detection of cell nuclei stained with DAPI.

Figure 13B:
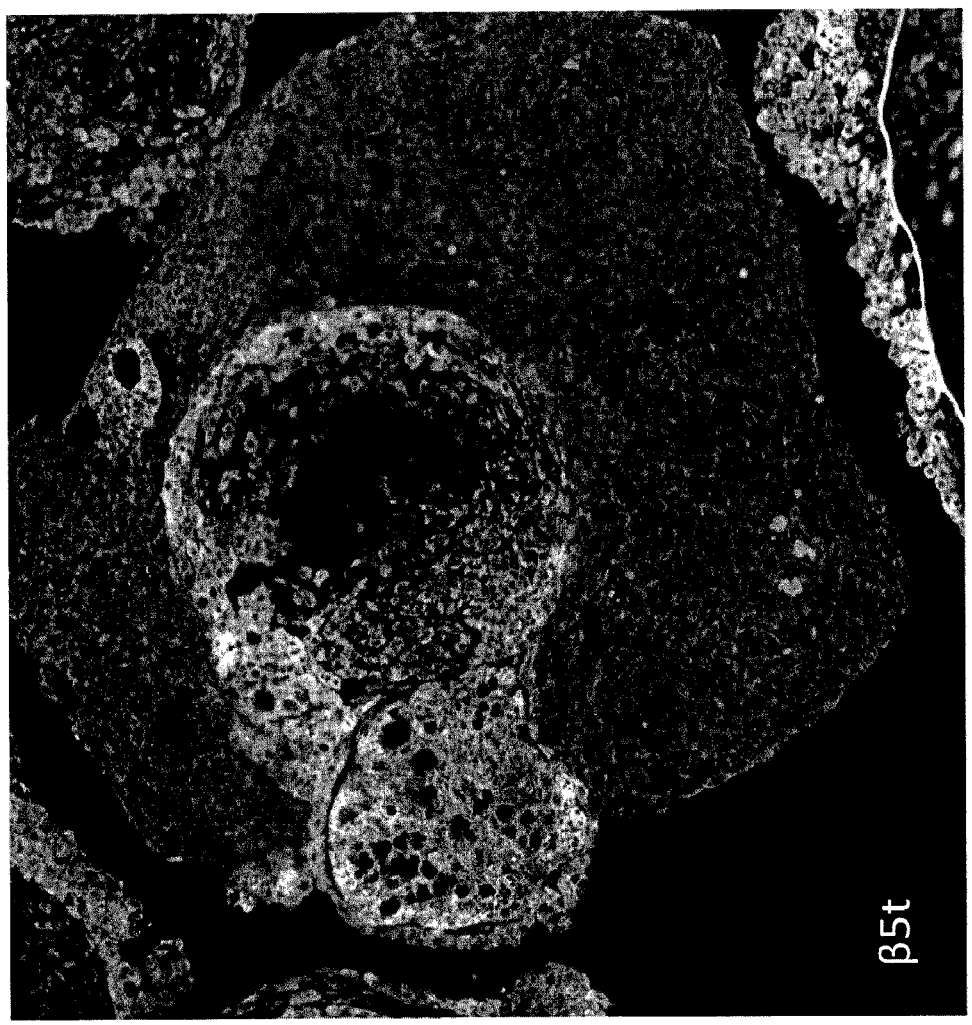

FIG. 13B is an image of the same hiPSC-derived organoid taken via confocal microscope, shown in FIG. 13A, illustrating the detection of thymoproteosome β5t antibodies conjugated with ALEXA FLUOR secondary antibodies.

Figure 14A:
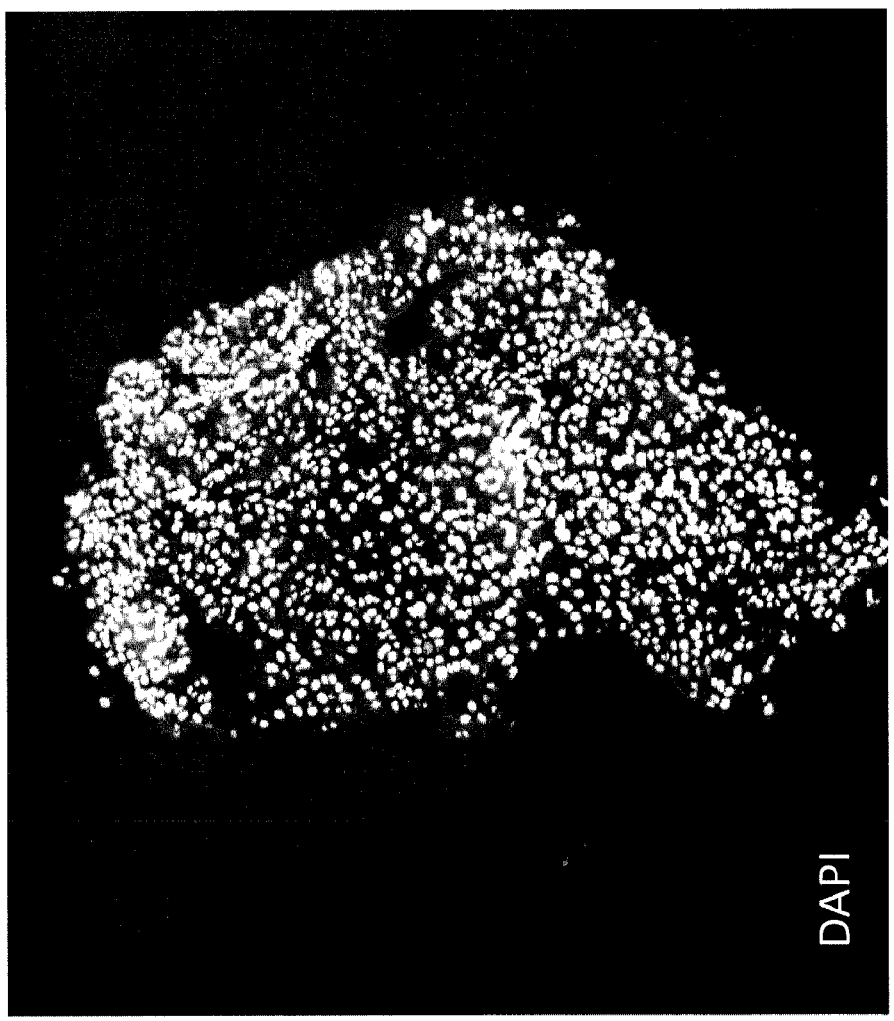

FIG. 14A is an image of an hiPSC-derived organoid taken via confocal microscope after 42 days of 3D culture, illustrating the detection of cell nuclei stained with DAPI.

Figure 14B:
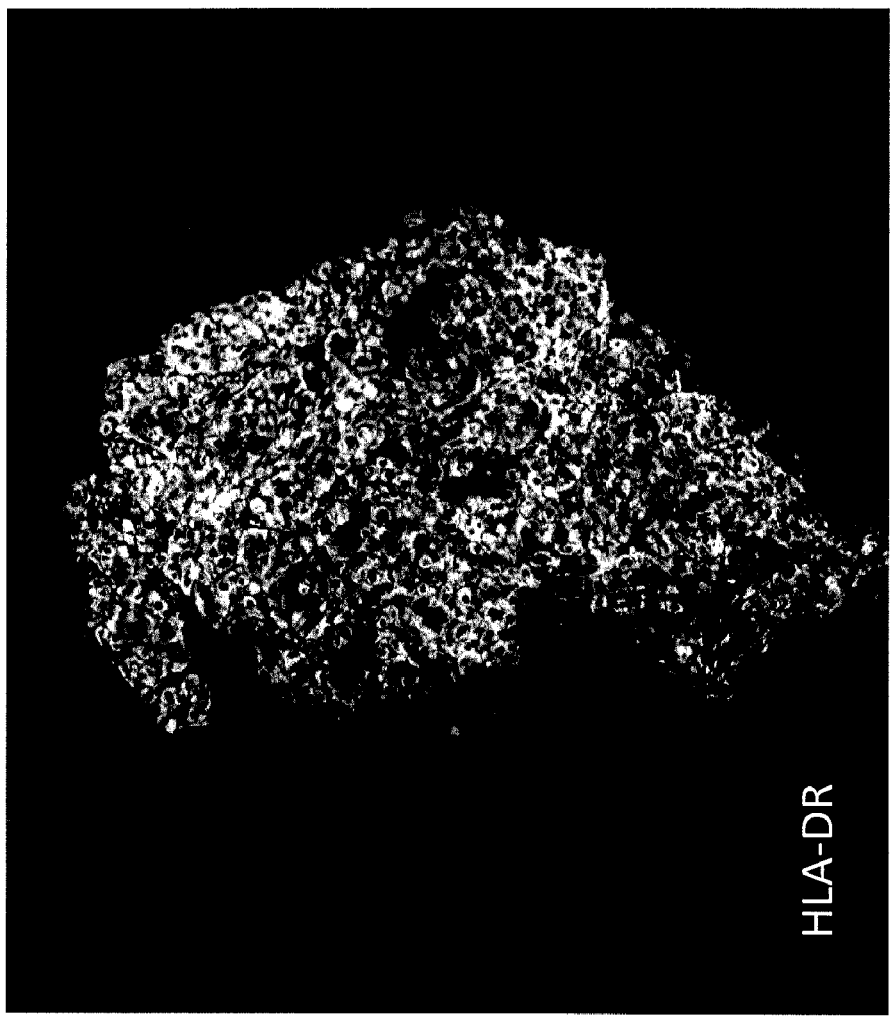

FIG. 14B is an image of the same hiPSC-derived organoid taken via confocal microscope shown in FIG. 14A, illustrating the detection of anti-HLA-DR antibodies conjugated with ALEXA FLUOR secondary antibodies.

Figure 15A:
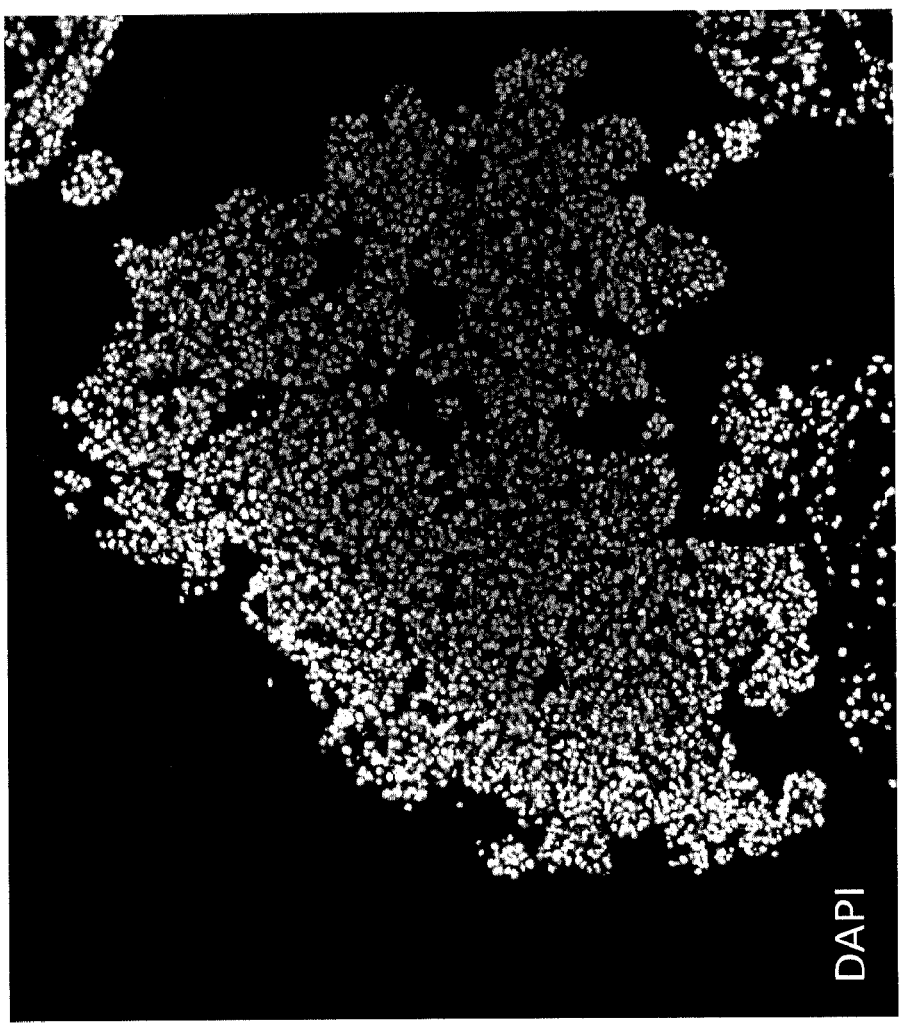

FIG. 15A is an image of an hiPSC-derived organoid taken via confocal microscope after 42 days of 3D culture, illustrating the detection of cell nuclei stained with DAPI.

Figure 15B:
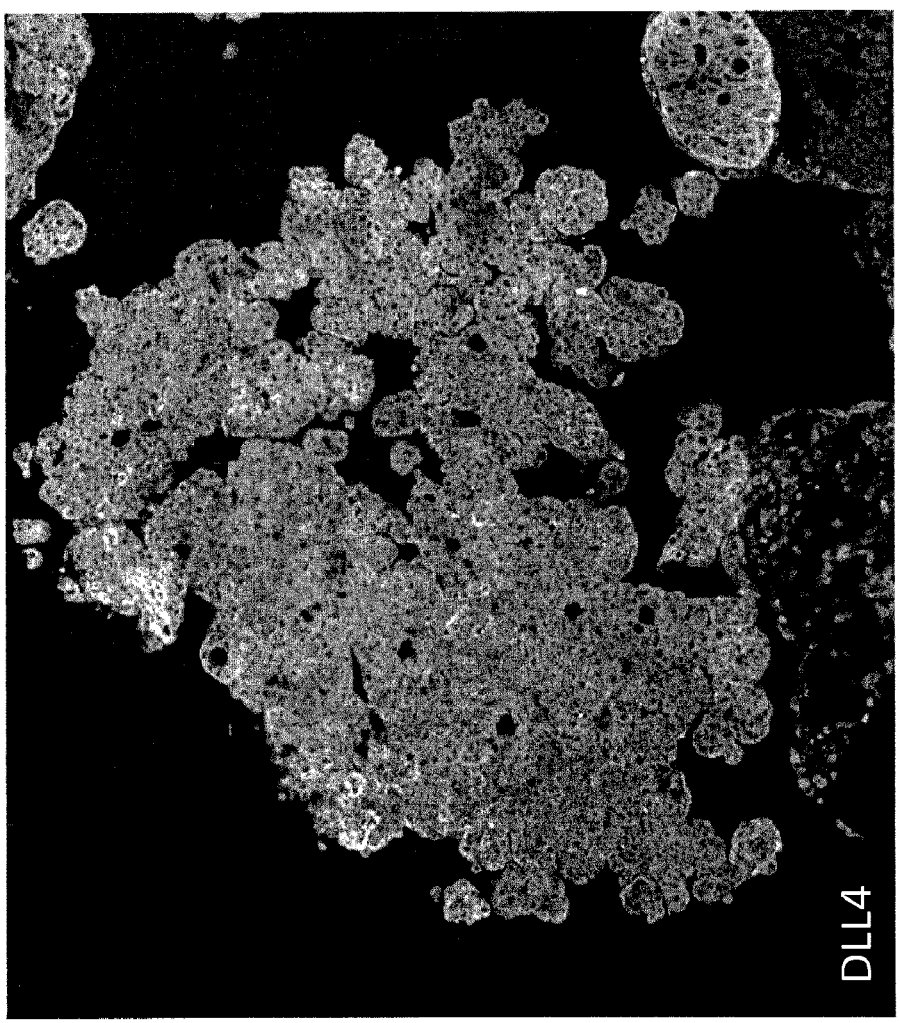

FIG. 15B is an image of the same hiPSC-derived organoid taken via confocal microscope shown in FIG. 15A, illustrating the detection of anti-DLL4 antibodies conjugated with ALEXA FLUOR secondary antibodies.

Figure 16A:
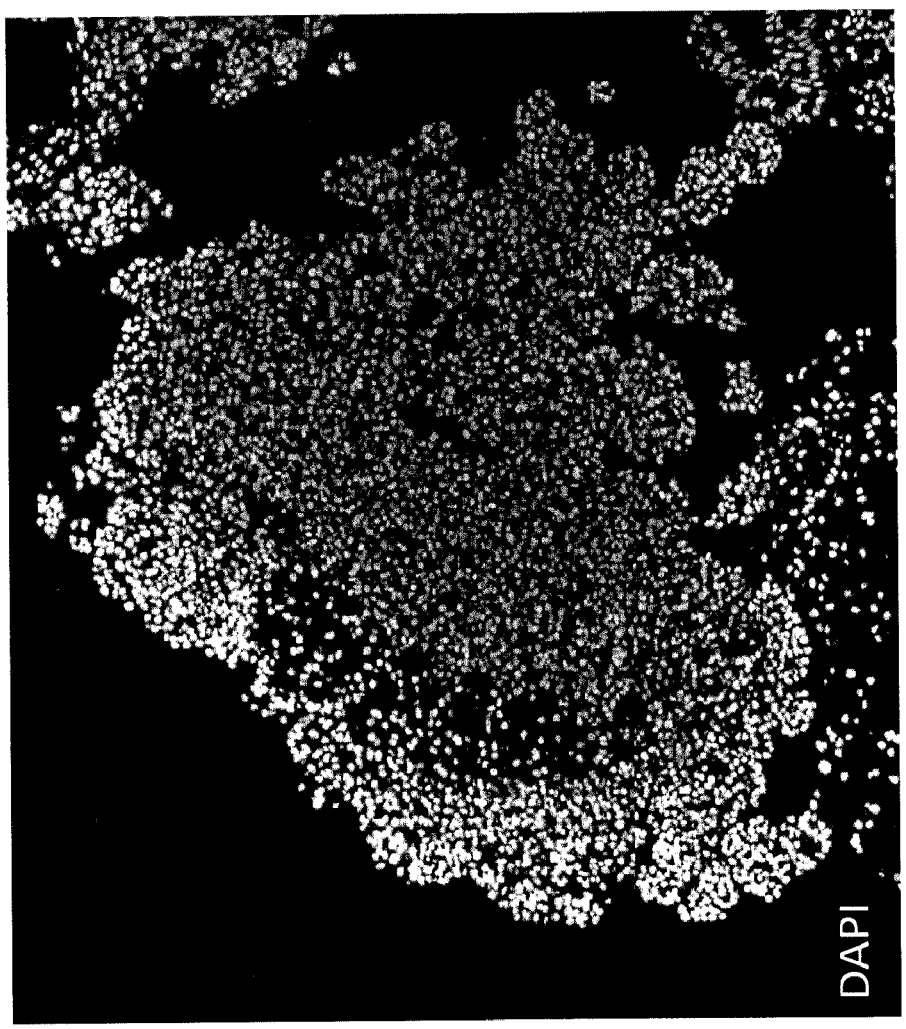

FIG. 16A is an image of the hiPSC-derived organoid taken via confocal microscope after 42 days of 3D culture, shown in FIG. 14A, illustrating the detection of cell nuclei stained with DAPI. The slide prepared for this image is of a different tissue cut of the organoid as compared to the tissue cut shown in FIG. 14A.

Figure 16B:
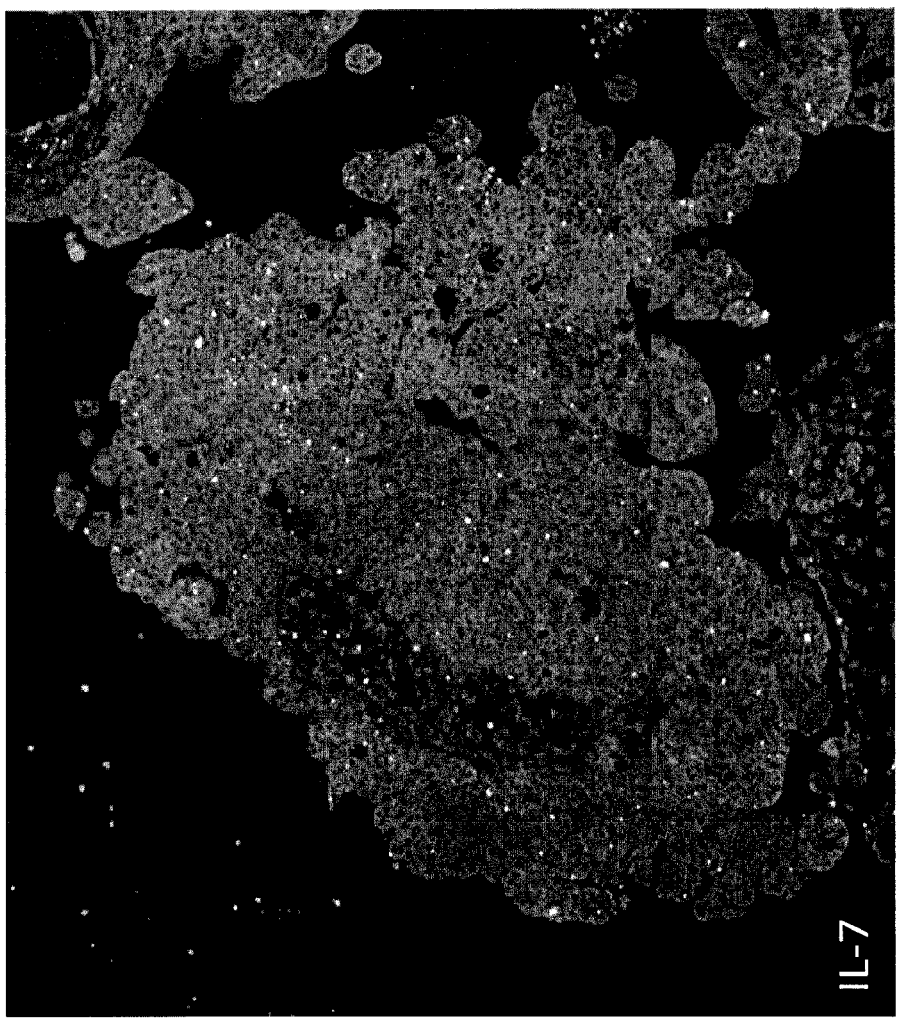

FIG. 16B is an image of the hiPSC-derived organoid taken via confocal microscope shown in FIG. 16A, illustrating the detection of anti-IL-7 antibodies conjugated with ALEXA FLUOR secondary antibodies.

DETAILED DESCRIPTION OF THE INVENTION

An embodiment of the invention provides a method of preparing a thymic organoid in vitro. An organoid is an in vitro, three-dimensional, miniature version of an organ. Thymic organoids produced by the inventive methods may mimic the physiology and function of a human thymus. Embodiments of the invention may provide any one or more of a variety of advantages. For example, human iPS (induced pluripotent stem cell) derived thymic organoids (hiTO) produced by the inventive methods may produce cells of the T-cell lineage (e.g., thymic emigrant cells) which may be useful for treating or preventing a condition in a mammal, e.g., cancer. Alternatively or additionally, the inventive methods may provide an organoid that can mimic the positive selection processing that takes place in the thymus. The positive selection process refers to the ability of newly formed thymocytes to recognize and interact with MHC (major histocompatibility complex). During positive selection in the human thymus, only thymocytes that can bind to MHC will survive, migrate into the medulla, and differentiate into mature T cells. Embodiments of the inventive method may produce thymic epithelial cells in a 3-dimensional (3D) organization resembling the human thymus. In embodiments, the inventive method may produce an organoid having the machinery capable of differentiating T cells in vitro. In embodiments, the invention may provide a way to produce autologous T cells. Embodiments of the invention may provide methods of generating T and NKT cell products for rare blood types for blood banking and the treatment of conditions, e.g., anemias and other cytopenias. In some embodiments, the inventive method may generate T and NKT cells for patients with immunodeficiencies.

In an embodiment the inventive method may comprise differentiating pluripotent stem cells into definitive endodermal cells in vitro. In this regard, the method may comprise culturing the pluripotent stem cells for a time and under conditions sufficient to differentiate the pluripotent stem cells into definitive endodermal cells. For example, the method may comprise culturing the pluripotent stem cells in the presence of members of the TGFβ superfamily for a period of about three to about six days, e.g., for a period of about five days. Suitable members of the TGFβ superfamily which may be useful in the inventive method include, e.g., activin A, or a combination of Wnt family member 3A (Wnt3A), bone morphogenic protein 4 (BMP4), and fibroblast growth factor (FGF). In an embodiment, the method may comprise culturing the pluripotent stem cells in the presence of activin A for a period of about three to about six days, e.g., for a period of about five days.

Alternatively or additionally, differentiating pluripotent stem cells into definitive endodermal cells in vitro may comprise culturing the pluripotent stem cells in the presence of suitable small molecules, such as, e.g., RhoK inhibitor, or iDE1 (Inducer of definitive endoderm 1) on PCL poly(E-caprolactone, a nanofibrous scaffold). In an embodiment, the method may comprise culturing the pluripotent stem cells in the presence of RhoK inhibitor for a period of about three to about six days, e.g., for a period of about five days.

In another embodiment, differentiating pluripotent stem cells into definitive endodermal cells in vitro may comprise, for example, targeting genes that are upstream or downstream in the activin pathway.

Suitable pluripotent stem cells may be any pluripotent stem cells. Pluripotent stem cells have the capacity to give rise to any of the three germ layers: endoderm, mesoderm, and ectoderm. Pluripotent stem cells may comprise, for example, stem cells, e.g., embryonic stem cells, nuclear transfer derived embryonic stem cells, induced pluripotent stem cells (iPSC), etc. The pluripotent stem cells may have a stem cell phenotype including (i) the ability to self-renew and (ii) pluripotency. For example, the pluripotent stem cells, e.g., iPSCs may be morphologically indistinguishable from embryonic stem cells (ESCs). For example, the pluripotent stem cells, e.g., iPSCs may have any one or more of a round shape, large nucleolus and small volume of cytoplasm. Alternatively or additionally, the pluripotent stem cells, e.g., iPSCs may be any one or more of mitotically active, actively self-renewing, proliferating, and dividing. Alternatively or additionally, the pluripotent stem cells, e.g., iPSCs, may express any one or more of a variety of pluripotency-associated genes. Pluripotency-associated genes may include, but are not limited to, Oct-3/4, Sox2, Nanog, GDF3, REX1, FGF4, ESG1, DPPA2, DPPA4, hTERT and SSEA1. Alternatively or additionally, the pluripotent cells, e.g., iPSCs, may express any one or more of a variety of pluripotency-associated markers. For example, human iPSCs may express any one or more of the markers SSEA-3, SSEA-4, TRA-1-60, TRA-1-81, TRA-2-49/6E, and Nanog. Mouse iPSCs may express the marker SSEA-1.

In an embodiment, the inventive method may comprise culturing the pluripotent stem cells in mammalian cellular basement matrix for at least one day prior to differentiating the pluripotent stem cells into endodermal cells in vitro. An example of a mammalian cellular basement matrix which may be useful in the inventive method is MATRIGEL membrane matrix (BD Biosciences, Franklin Lakes, NJ). In an embodiment of the invention, the mammalian cellular basement comprises a RhoK inhibitor. In an embodiment of the invention, the cellular basement matrix comprises medium suitable for culturing pluripotent stem cells (e.g., ESSENTIAL 8 medium (Gibco, Waltham, MA)). Without being bound to a particular theory or mechanism, it is believed that culturing the pluripotent stem cells in mammalian cellular basement matrix with an RhoK inhibitor for at least one day prior to differentiating the pluripotent stem cells into endodermal cells in vitro may reduce or prevent apoptosis of the cells.

In an embodiment, the method comprises differentiating the endodermal cells into third PPE cells in vitro. In this regard, the method may comprise culturing the endodermal cells for a time and under conditions sufficient to differentiate the endodermal cells into third PPE cells. For example, the method may comprise culturing the endodermal cells in the presence of one or more of retinoic acid, wnt/catenin signaling inhibitors such as IWR-1, or related small chemicals such as, e.g., JW67, JW74, NSC668036, AMBMP hydrochloride, FH535, Cardionogen 1, IWP4, PNU 74654, iCRT14, KY02111, ICG001, and CCT 031374 hydrobromide for a period of about three to about six days, e.g., for a period of about five days. Alternatively or additionally, the method may comprise culturing the endodermal cells in the presence of aptamers and/or antibodies to inhibit the wnt/catenin pathway or the inhibition of genes upstream or downstream in the wnt/catenin pathway for a period of about three to about six days, e.g., for a period of about five days. In an embodiment, the method may comprise culturing the endodermal cells in the presence of retinoic acid and IWR-1 for a period of about three to about six days, e.g., for a period of about five days. The third pharyngeal pouch is a structure which gives rise to part of the thymic epithelium in the human thymus. The pharyngeal pouches are transient embryonic structures and give rise to craniofacial organs, including the thymus and parathyroid glands. The prospective thymus and parathyroid are marked by the expression of the transcription factors Foxnl and Gcm2, respectively.

In an embodiment, the method comprises differentiating the third PPE cells into TEPLCs in vitro. In this regard, the method may comprise culturing the third PPE cells for a time and under conditions sufficient to differentiate the third PPE cells into TEPLCs. For example, the method may comprise culturing the third PPE cells in the presence of one or more molecules in the Wnt pathway, e.g., Wnt3a and Wnt4, and/or members of the TGF superfamily, e.g., BMP2, BMP3, BMPS, BMP6, BMP7, activin, TGFP, and/or inhibin, or agents which trigger or inhibit related pathways, for a period of about three to about six days. In an embodiment, the method may comprise culturing the third PPE cells in the presence of BMP4 and Wnt3a for a period of about three to about six days, e.g., for a period of about five days.

In an embodiment of the invention, the TEPLCs are keratin $5^+$/keratin $8^+$/FOXN1$^-$. In an embodiment of the invention, the TEPLCs are keratin $5^+$/keratin $8^+$/FOXN1$^-$/β5$^-$. Most of the cells in the human thymus express Keratin 5 and Keratin 8. The population of cells with high Keratin 5 and high Keratin 8 expression is referred to as the TEC bipotent or progenitor region. Without being bound to a particular theory or mechanism, it is believed that the keratin $5^+$/keratin $8^+$ TEC bipotent or progenitor region gives rise to the thymic cortex and thymic medulla.

In another embodiment, the inventive method comprises (i) differentiating pluripotent stem cells into endodermal cells in vitro; (ii) differentiating the endodermal cells into third PPE cells in vitro; and/or (iii) differentiating the third PPE cells into TEPLCs in vitro, without dissociating the cells. In a preferred embodiment, the method comprises differentiating the third PPE cells into TEPLCs in vitro without dissociating the cells.

In an embodiment, the method comprises differentiating the TEPLCs into TEPCs in an in vitro, three-dimensional culture. In this regard, the method may comprise culturing the TEPLCs for a time and under conditions sufficient to differentiate the TEPLCs into TEPCs. For example, the method may comprise culturing the TEPLCs in TEC expansion medium. The TEC expansion medium may comprise, for example, EBMB, B27 serum replacement, hydrocortisone, cholera toxin B, and human epidermal growth factor (EGF). The TEC expansion medium may comprise additional factors. The additional factors may comprise, for example, Wnt3a, FGF7, and BMP4. The TEPLCs may be cultured for a period of about 60 days to about 150 days, or a period of about six to about 60 days, or a period of about 20 to about 45 days, e.g., for a period of about seven days or 42 days. The culturing period is not limited and may be, for example, months. Culturing the TEPLCs may result in a three-dimensional spheroid which may be located, e.g., in the center of multilayered regions of TEPLCs. A portion of the spheroid may be removed and transferred to a 3D culture where the cells may further differentiate into TEPCs. The TEPC population within the mouse fetal thymus has been defined with several surface markers, including K5+K8+ TECs, pan-cytokartin+EpCAM+ or pan-cytokartin+ MTS24+ or EpCAM1+MTS24+, MTS20+, EpCAM1+ CD205+CD40−, and Claudin3/4loUEA1−.

Without being bound to a particular theory or mechanism, it is believed that 3D culture may be more effective for facilitating thymic organoid development as compared to two dimensional (2D) culture, e.g., 2D culture of thymic stromal cells in monolayer cultures (TSMCs). Suitable 3D culture systems may include any 3D culture system, for example, hanging drop plates and ultra-low attachment multiwell plates. Hanging drop plates are commercially available such as, for example, the PERFECTA3D hanging drop plate, available from Biospherix, Parish, NY Ultra-low attachment multiwell plates are also commercially available such as, for example, AGGREWELL ultra-low attachment, multi-well plate, available from Stemcell Technologies, Vancouver, Canada.

In an embodiment, the method comprises differentiating the TEPCs into TECs in an in vitro, three-dimensional culture in the presence of BMP4. In this regard, the method may comprise culturing the TEPCs for a time and under conditions sufficient to differentiate the TEPCs into TECs. In an embodiment, the inventive method comprises differentiating the TEPCs into TECs in the in vitro, three-dimensional culture in the presence of one or more of BMP4, Wnt3a and fibroblast growth factor 7 (FGF7). Preferably, the method comprises differentiating the TEPCs into TECs in the in vitro, three-dimensional culture in the presence of all of BMP4, Wnt3a and FGF7. As used herein, "Wnt3a" refers to Wnt family member 3A. The WNT gene family includes structurally related genes which encode secreted signaling proteins involved in certain epithelial morphological processes including epithelial-mesenchymal transition.

During embryonic development there is a minor population of TECs co-expressing cytokeratin5 and cytokeratin8, indicating the existence of progenitor cells (TEPCs) that may give rise to both cortical and medullary TECs. Several lines of evidence support the presence of the common precursors by showing that all the epithelial cells of the third pharyngeal pouch at E10.5 express both 4F1 and IVC4 which mark the cTECs and mTECs, respectively. Human TECs produce BMP4 and both thymocytes and thymic epithelium express the molecular machinery involved in a response to this protein. Additionally, cortical thymic epithelial cells (cTECs) in the human thymus provide the differentiation signal, regulate the directional migration and population expansion of immature T lymphocytes, and positively select $CD4^+CD8^+$ thymocytes, which are capable of recognizing self-major histocompatibility complex (MHC). The epithelial component of the thymus (the TECs) ultimately gives rise to the medulla of the human thymus. TECs form the basic three-dimensional architecture that facilitates T-cell differentiation and maturation from common lymphoid progenitors. The proper differentiation and organization of different TECs is involved in both thymocyte development and T-cell repertoire selection. TEC-associated genes may include, but are not limited to, subunit beta-5t (encoded by Pmsb11), Ly-51/CD249 (Enpep), delta-like ligand 4 (Dll4), and serine protease 16 (Prss16) and CD205 (DEC-205, Ly75).

In an embodiment, the inventive method may comprise forming the TECs into a thymic organoid in the in vitro, three-dimensional culture. The thymic organoid may express any one or more of β5t, DLL4, and interleukin 7. As used herein, the term "β5t" refers to a genetic marker expressed exclusively in cortical thymic epithelial cells, which are involved in the positive selection of developing thymocytes. As used herein, the term "DLL4" refers to delta like canonical Notch ligand 4. The delta gene family encodes Notch ligands that are characterized by a DSL domain, EGF repeats, and a transmembrane domain. As used herein, the term "interleukin 7" or "IL-7" refers to a growth factor secreted by the thymus, which is involved in human T-cell development.

In an embodiment of the invention, the method may comprise transferring a collection of (i) younger, less differentiated TEPLCs and (ii) older, more differentiated cells (e.g., TEPCs or TECs) together to a three-dimensional culture and culturing the cells in the three dimensional culture to form a thymic organoid (FIG. 6). The younger, less differentiated TEPLCs may surround the older, more differentiated cells (e.g., TEPCs or TECs) in a 3D spheroid. Without being bound to a particular theory or mechanism, it is believed that the older, more differentiated cells forming the spherical structures can be more differentiated than the lower layer of younger, less differentiated cells. The older, more differentiated cells may become exhausted after continuous expansion. Since the lower layer of cells is less differentiated, it is believed that they may contribute to the late stage of organoid growth.

While the inventive method may comprise co-culturing cells with mesenchyme or stromal cells, in a preferred embodiment, the inventive method does not comprise co-culturing the cells with mesenchyme or stromal cells. In this regard, the inventive method does not comprise co-culturing any of the cells of the inventive method, namely, the pluripotent stem cells, endodermal cells, third PPE cells, TEPLCs, TEPCs, TECs, or the thymic organoid with mesenchyme or stromal cells. As used herein, the term "mesenchyme" refers to a type of tissue comprised of loose cells embedded in the extracellular matrix. The mesenchyme provides a determinative role in defining the organ-specific features of a developing organ through cell contact and short-acting factors. Mesenchyme forms before the primary germ layers develop and cell populations lose their adhesive properties and detach from sheets of epithelia. This process, referred to as an epithelial-mesenchymal transition, gives rise to the mesodermal layer of the embryo. Epithelial-mesenchymal transitions play roles in cellular proliferation and tissue repair, and are indicated in many pathological processes. In an embodiment, the inventive method does not comprise co-culturing the cells with mesenchymal stem cells. In this regard, the inventive method does not comprise co-culturing any of the cells in the inventive method, namely, the pluripotent stem cells, endodermal cells, third PPE cells, TEPLCs, TEPCs, TECs, or the thymic organoid with mesenchymal stem cells.

As used herein, the term "stromal cells" refers to progenitors of skeletal tissue components such as bone, cartilage, the hematopoiesis-supporting stroma, and adipocytes.

Stromal cells may be experimentally induced to undergo differentiation into various cell types. Additionally, stromal cells may be generated from embryonic stem cells (ESC) and induced pluripotent stem cells (iPSC).

In an embodiment, the inventive method does not comprise passaging the cells. In this regard, any one or more of (i) differentiating pluripotent stem cells into endodermal cells in vitro; (ii) differentiating the endodermal cells into third PPE cells in vitro; (iii) differentiating the third PPE cells into TEPLCs in vitro; (iv) differentiating the TEPLCs into TEPCs in an in vitro, three-dimensional culture; (v) differentiating the TEPCs into TECs in the in vitro, three-dimensional culture in the presence of BMP4; and (vi) forming the TECs into a thymic organoid in the in vitro, three-dimensional culture does not comprise passaging the cells. Passaging is a common manipulation carried out in culturing cells. Passaging (also referred to as subculture, expanding or splitting cells) involves transferring a small number of cells into a new vessel. Passaging allows cells to be cultured for a longer time if they are split regularly, as it avoids the senescence associated with prolonged high cell density. For adherent cultures, passaging involves dissociating the cells. Passaging is commonly done with a mixture of trypsin-EDTA or other enzyme mixes. Passaging may involve seeding a new culture with a small number of dissociated cells. In an embodiment, the inventive method avoids passaging and dissociating the cells.

In an embodiment, the inventive method is carried out in xeno-free medium. As used herein the term "xeno-free" refers to an absence of direct or indirect exposure to non-human animal components. Advantages of xeno-free medium include the absence of potential contaminants and improved consistency in both performance and quality of the culture medium. In this regard, any one or more of (preferably, all of) (i) differentiating pluripotent stem cells into endodermal cells in vitro; (ii) differentiating the endodermal cells into third PPE cells in vitro; (iii) differentiating the third PPE cells into TEPLCs in vitro; (iv) differentiating the TEPLCs into TEPCs in an in vitro, three-dimensional culture; (v) differentiating the TEPCs into TECs in the in vitro, three-dimensional culture in the presence of BMP4; and (vi) forming the TECs into a thymic organoid in the in vitro, three-dimensional culture is carried out in xeno-free medium.

In an embodiment, the inventive method may comprise carrying out any one or more of: (i) differentiating pluripotent stem cells into endodermal cells in vitro; (ii) differentiating the endodermal cells into third PPE cells in vitro; (iii) differentiating the third PPE cells into TEPLCs in vitro; (iv) differentiating the TEPLCs into TEPCs in an in vitro, three-dimensional culture; (v) differentiating the TEPCs into TECs in the in vitro, three-dimensional culture in the presence of BMP4; and (vi) forming the TECs into a thymic organoid in the in vitro, three-dimensional culture in the presence of one or more Mesenchymal Stem Cell (MSC) factors. Preferably, the method comprises differentiating the TEPLCs into TEPCs in the presence of one or more MSC factors. MSC factors may be isolated or purified from MSC and mesenchyme. MSC factors may include, but are not limited to, one or more of fibroblast growth factor 7 (FGF7, or KGF7), bone morphogenetic protein 4 (BMP4), Protein Wnt-3a (Wnt3a), fibroblast growth factor 10 (FGF10), insulin-like growth factor-1 (IGF-1), fibroblast growth factor 8 (FGF8), transforming growth factor (TGFβ$_{inh}$), and cyclopamine. Preferably, the one or more MSC factors comprise FGF10, IGF-1, FGF8, TGFP inhibitor and cyclopamine.

In other embodiments, the inventive method may comprise culturing the thymic organoid to overexpress one or more autologous proteins involved in T cell differentiation. In certain embodiments, the one or more autologous proteins involved in T cell differentiation comprise one or more of DLL4 and IL-7. In embodiments, the inventive method may comprise culturing the thymic organoid with one or more molecules, antibodies, or drugs involved in T cell differentiation. The one or more molecules, antibodies, or drugs involved in T cell differentiation may include, for example, Il-7, Flt3L, SCF, IL-2, IL-1b, IFN, ascorbic acid, T cell activation antibodies (anti Cd-3, anti TCRa or TCRb, anti CD28, anti CD49d, among others), and/or immunosuppressive drugs.

Another embodiment of the invention provides a thymic organoid produced by any of the inventive methods described herein with respect to other aspects of the invention.

In an embodiment, the thymic organoid produced by the inventive method comprises keratin 5+/keratin 8+/FOXN1+ cells. The transcription factor forkhead box N1 (FOXN1) is involved in the development of thymic epithelial cells.

In an embodiment, the thymic organoid produced by the inventive method may comprise keratin 5+/keratin 8+/thymoproteosome β5t+cells. As noted above, β5t is involved in the positive selection of developing thymocytes. Also as noted above, without being bound to a particular theory or mechanism, it is believed that the keratin $5^+$/keratin $8^+$ TEC bipotent or progenitor region gives rise to the thymic cortex and thymic medulla in human thymus.

In certain embodiments, the thymic organoid comprises keratin $5^{high}$/keratin $8^{low}$ cells.

In certain embodiments, the thymic organoid comprises keratin $5^{low}$/keratin $8^{high}$ cells.

As used herein, the term "positive" (which may be abbreviated as "+"), with reference to expression of the indicated cell marker, means that the cell expresses the indicated cell marker at any detectable level, which may include, for example, expression at a low (but detectable) level as well as expression at a high (hi) level. The term "negative" (which may be abbreviated as "−"), as used herein with reference to expression of the indicated cell marker, means that the cell does not express the indicated cell marker at a detectable level. The term "high" (which may be abbreviated as "hi"), as used herein with reference to expression of the indicated cell marker, refers to a subset of cells that are positive for expression of the indicated cell marker which stain more brightly for the indicated cell marker using immunohistochemical methods (e.g., FACS, flow cytometry, immunofluorescence assays and microscopy) than other cells that are positive for expression of the indicated cell marker. For example, cells with a "high" level of expression of the indicated cell marker may stain more brightly than about 50%, about 60%, about 70%, about 80%, about 90%, or about 95%, or a range of any two of the foregoing values, of the other cells that are positive for expression of the indicated cell marker. The term "low," as used herein with reference to expression of the indicated cell marker, refers to a subset of cells that are positive for expression of the indicated cell marker which stain less brightly for the indicated cell marker using immunohistochemical methods than other cells that are positive for expression of the indicated cell marker. For example, cells with a "low" level of expression of the indicated cell marker may stain less brightly than about 50%, about 60%, about 70%, about 80%, about 90%, or about 95%, or a range of any two of the foregoing values, of the other cells that are positive for expression of the indicated cell marker.

The thymic organoid produced by the inventive methods may be useful for generating cells of the T cell lineage (e.g., thymic emigrant cells) for adoptive cell therapy. Accordingly, an embodiment of the invention provides a method of preparing thymic emigrant cells in vitro.

The method may comprise migrating progenitor cells into the inventive thymic organoid. For example, any progenitor cells which have the potential to develop into the T cell lineage may be suitable to migrate into the inventive thymic organoid. Examples of suitable progenitor cells may include primitive mesoderm cells, hematopoietic progenitors, pluripotent stem cell-derived cells, hematopoietic stem cells, T cell progenitors, double positive T cells, and immature T cell lineage cells. In an embodiment, migrating progenitor cells may involve seeding the progenitor cells into the thymic organoid.

The method may further comprise migrating support cells into the thymic organoid. Support cells which may be suitable to migrate into the inventive thymic organoid may comprise, for example, mesenchymal stem cells or any other cell that commonly exists in the thymus and is not directly produced from TEPCs. Examples of suitable support cells that are not directly produced from TEPCs include, for example, endothelial cells and dendritic cells, among others. Migrating support cells may involve seeding the support cells into the thymic organoid.

The method of preparing the thymic emigrant cells may comprise egressing the cells from the thymic organoid, wherein the cells egressing from the thymic organoid are thymic emigrant cells. The egressing of the cells from the thymic organoid may be observed under direct visualization using, for example, a dissecting microscope. The cells may begin to egress from the thymic organoid about 2 to about 5 days after seeding and may continue to egress for about four to about five weeks or more. It is believed that the cells may continue to egress for several months or more.

The method of preparing the thymic emigrant cells may comprise isolating the thymic emigrant cells from the thymic organoid. Isolating the thymic emigrant cells from the thymic organoid may be carried out in any suitable manner. For example, the method may comprise gently removing the egressing cells by removing the media from the 3D culture of the thymic organoid, e.g., the hanging drop (e.g., by pipetting). Preferably, the isolating of the thymic emigrant cells from the thymic organoid may be carried out under direct visualization using, for example, a dissecting microscope. Preferably, the thymic emigrant cells are isolated without aspirating or disrupting the thymic organoid. The method may comprise replacing the media that was removed from the thymic organoid culture with fresh media. The thymic organoid may, subsequently, be observed for the egress of further thymic emigrant cells.

The thymic emigrant cells may be $CD8\alpha^+CD8\beta^+CD4^-$ or $CD8\alpha^-CD8\beta^-CD4^+$. Alternatively or additionally, the thymic emigrant cells are any one or more of $CCRX4^-$, $CD3^+$, $CD69^-$, $MHC-I^+$, $CD62L^+$, and $CCR7^+$. Preferably, the thymic emigrant cells are all of $CCRX4^-$, $CD3^+$, $CD69^-$, $MHC-I^+$, $CD62L^+$, and $CCR7^+$. Alternatively or additionally, the thymic emigrant cells are $TCR\alpha^+TCR\beta^+$. Preferably, the thymic emigrant cells are $TCR\alpha^+TCR\beta^+$.

The method may further comprise differentiating the thymic emigrant cells into any desired type of cell of the T cell lineage. Examples of cell types which may be prepared by differentiating the thymic emigrant cells include, but are not limited to, natural killer T (NKT) cells, T cells (e.g., naïve T cells, regulatory T-cells, T stem cell memory cells, effector T cells, effector memory RA cells (EMRA), Th1 cells, Th2 cells, or Th17 cells).

The inventive method may produce an isolated or purified population of thymic emigrant cells. The thymic emigrant cells prepared by the inventive methods may be useful for preparing cells for adoptive cell therapies. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

Another embodiment of the invention may provide an isolated or purified population of cells. The population of thymic emigrant cells can be a heterogeneous population comprising the thymic emigrant cells in addition to a cell other than a thymic emigrant cell, e.g., a PBMC, a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of (e.g., consisting essentially of) thymic emigrant cells. In an embodiment of the invention, about 1% to about 100%, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or a range defined by any two of the foregoing values, of the population of cells comprises thymic emigrant cells.

In an embodiment of the invention, the thymic emigrant cells are expanded in vitro. Expansion of the numbers of cells can be accomplished by any of a number of methods as are known in the art as described in, for example, U.S. Pat. Nos. 8,034,334; 8,383,099; and U.S. Patent Application Publication No. 2012/0244133. For example, expansion of the numbers of cells may be carried out by culturing the cells with OKT3 antibody, IL-2, and feeder PBMC (e.g., irradiated allogeneic PBMC). In another embodiment of the invention, the thymic emigrant cells are not expanded in vitro prior to the administration to a mammal.

In an embodiment of the invention, the thymic emigrant cells are $CD8\alpha+CD8\beta+CD4-$ or $CD8\alpha-CD8\beta-CD4+$ after antigen stimulation and after expansion of the numbers of thymic emigrant cells.

The populations of thymic emigrant cells can be formulated into a composition, such as a pharmaceutical composition. In this regard, a pharmaceutical composition may comprise any of the populations of thymic emigrant cells described herein and a pharmaceutically acceptable carrier. The pharmaceutical composition can comprise a population of thymic emigrant cells in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular population of cells under consideration. Such pharmaceutically acceptable carriers are well-known to those skilled in the art and are readily available to the public.

It is preferred that the pharmaceutically acceptable carrier be one which has no detrimental side effects or toxicity under the conditions of use.

The choice of carrier will be determined in part by the particular population of thymic emigrant cells, as well as by the particular method used to administer the population of thymic emigrant cells. Accordingly, there are a variety of suitable formulations of the pharmaceutical composition of the invention. Suitable formulations may include any of those for parenteral, subcutaneous, intratumoral, intravenous, intramuscular, intraarterial, intrathecal, or interperitoneal administration. More than one route can be used to administer the population of thymic emigrant cells, and in certain instances, a particular route can provide a more immediate and more effective response than another route.

Preferably, the population of thymic emigrant cells is administered by injection, e.g., intravenously. When the population of thymic emigrant cells is to be administered, the pharmaceutically acceptable carrier for the thymic emigrant cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumin.

For purposes of the invention, the amount or dose of the population of thymic emigrant cells or pharmaceutical composition administered (e.g., numbers of cells when the population of cells is administered) should be sufficient to effect, e.g., a therapeutic or prophylactic response, in the patient over a reasonable time frame. For example, the dose of the population of cells or pharmaceutical composition should be sufficient to treat or prevent a condition in a period of from about 2 hours or longer, e.g., 12 to 24 or more hours, from the time of administration. In certain embodiments, the time period could be even longer. The dose will be determined by the efficacy of the particular population of cells or pharmaceutical composition administered and the condition of the patient, as well as the body weight of the patient to be treated.

Many assays for determining an administered dose are known in the art. For purposes of the invention, an assay, which comprises comparing the extent to which target cells are lysed upon administration of a given dose of such thymic emigrant cells to a mammal among a set of mammals of which is each given a different dose of the cells, could be used to determine a starting dose to be administered to a patient. The extent to which target cells are lysed upon administration of a certain dose can be assayed by methods known in the art.

The dose of the population of cells or pharmaceutical composition also will be determined by the existence, nature and extent of any adverse side effects that might accompany the administration of a particular population of cells or pharmaceutical composition. Typically, the attending physician will decide the dosage of the population of cells or pharmaceutical composition with which to treat each individual patient, taking into consideration a variety of factors, such as age, body weight, general health, diet, sex, population of cells or pharmaceutical composition to be administered, route of administration, and the severity of the condition being treated.

Any suitable number of thymic emigrant cells of the invention can be administered to a mammal. While a single thymic emigrant cell of the invention theoretically is capable of expanding and providing a therapeutic benefit, it is preferable to administer about $10^2$ or more, e.g., about $10^3$ or more, about $10^4$ or more, about $10^5$ or more, about $10^8$ or more, thymic emigrant cells. Alternatively, or additionally about $10^{12}$ or less, e.g., about $10^{11}$ or less, about $10^9$ or less, about $10^7$ or less, or about $10^5$ or less, thymic emigrant cells can be administered to a mammal. The number of thymic emigrant cells can be administered to a mammal in an amount bounded by any two of the above endpoints, e.g., about $10^2$ to about $10^5$, about $10^3$ to about $10^7$, about $10^3$ to about $10^9$, or about $10^5$ to about $10^{10}$. For example, about $10^7$ to about $10^8$ thymic emigrant cells may be administered. Without being bound to a particular theory or mechanism, it is believed that the thymic emigrant cells produced by the inventive methods may be more potent than exhausted tumor infiltrating lymphocytes (TILs).

An embodiment of the invention also provides a method of treating or preventing a condition in a mammal the method comprising: preparing the thymic emigrant cells in vitro and administering the thymic emigrant cells to the mammal in an amount effective to treat or prevent the condition in the mammal.

The method comprises administering to the mammal any of the populations of thymic emigrant cells described herein, or a pharmaceutical composition comprising any of the populations described herein, in an amount effective to treat or prevent the condition in the mammal. In an embodiment of the invention, the condition is a cancer, an immunodeficiency, an autoimmune condition, an infection, or a blood condition.

The cancer may be any cancer, including, for example, any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

The immunodeficiency may be any condition in which the body's ability to defend itself against outside pathogens is disrupted. The immunodeficiency may be any condition in which a patient's immune system is compromised and in need of reconstitution after immunodeployment due to irradiation or chemotherapy. Immunodeficiency may include, for example, a depleted adaptive immune system in the elderly population. Without being bound to a particular theory or mechanism, it is believed that the thymic organoid of the invention may produce thymic emigrant cells which may be useful for the treatment of both primary and secondary immunodeficiencies. Examples of immunodeficiencies which may be treated or prevented include, but are not limited to X-linked agammaglobulinemia (XLA), variable immunodeficiency (CVID), severe combined immunodeficiency (SCID), AIDS, and hepatitis.

The autoimmune condition may be any condition in which the body's immune system attacks healthy cells.

Without being bound to a particular theory or mechanism, it is believed that the thymic organoid of the invention may produce thymic emigrant cells which may be useful for the treatment of autoimmune conditions. Examples of autoimmune conditions which may be treated or prevented include, but are not limited to, rheumatoid arthritis, lupus, type 1 diabetes, multiple sclerosis, celiac disease, temporal arteritis, vasculitis, alopecia areata, ankylosing spondylitis, Sjögren's syndrome, and polymyalgia rheumatic.

The infection may be an infectious condition, for example, a viral condition, a bacterial condition, a fungal condition, or a protozoan condition. The cancer may be any of the cancers described herein with respect to other aspects of the invention.

For purposes herein, "viral condition" means a condition that can be transmitted from person to person or from organism to organism, and is caused by a virus. In an embodiment of the invention, the viral condition is caused by a virus selected from the group consisting of herpes viruses, pox viruses, hepadnaviruses, papilloma viruses, adenoviruses, coronaviruses, orthomyxoviruses, paramyxoviruses, flaviviruses, and caliciviruses. For example, the viral condition may be caused by a virus selected from the group consisting of respiratory syncytial virus (RSV), influenza virus, herpes simplex virus, Epstein-Barr virus, varicella virus, cytomegalovirus, hepatitis A virus, hepatitis B virus, hepatitis C virus, human immunodeficiency virus (HIV), human T-lymphotropic virus, calicivirus, adenovirus, and Arena virus.

The viral condition may be, for example, influenza, pneumonia, herpes, hepatitis, hepatitis A, hepatitis B, hepatitis C, chronic fatigue syndrome, sudden acute respiratory syndrome (SARS), gastroenteritis, enteritis, carditis, encephalitis, bronchiolitis, respiratory papillomatosis, meningitis, HIV/AIDS, and mononucleosis.

The blood condition may be any non-cancerous condition that affects the blood. The blood condition may be, for example, cytopenia (e.g., anemia, leukopenia, and neutropenia), bleeding disorders such as hemophilia, and blood clots.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a patient. Furthermore, the treatment or prevention provided by the inventive method can include treatment or prevention of one or more conditions or symptoms of the condition being treated or prevented. For example, treatment or prevention can include promoting the regression of a tumor. Also, for purposes herein, "prevention" can encompass preventing the recurrence of the condition, delaying the onset of the condition, or a symptom or condition thereof.

The term "mammal" as used herein refers to any mammal, including, but not limited to, mice, hamsters, rats, rabbits, cats, dogs, cows, pigs, horses, monkeys, apes, and humans. Preferably, the mammal is a human.

FIG. 9 illustrates examples of methods of treatment according to embodiments of the invention. In a first embodiment, with reference to FIG. 9, tumor reactive T-cells of a patient may be reprogrammed to T cell-derived induced pluripotent stem cells (hT-iPSC). Multiple colonies of human T-iPSCs may be grown in culture and may be differentiated into T-cell progenitors. The T-cell progenitors may be used to seed a thymic organoid prepared by any of the inventive methods described herein with respect to other aspects of the invention.

The thymic organoid may produce thymic emigrant cells (e.g., induced recent thymic emigrant cells (iRTE)) or nave T cells, which may then be re-introduced into the patient.

In another embodiment, with reference to FIG. 9, tumor reactive T-cells of a patient may be reprogrammed to hT-iPSC. Multiple colonies of hT-iPSCs may be grown in culture. The inventive methods of preparing a thymic organoid from the iPSCs may then be carried out, resulting in a thymic organoid. T cell progenitors may then be used to seed the thymic organoid, which may then produce iRTE or naïve T cells, which may then, in turn, be re-introduced into the patient, as shown in FIG. 9.

The following examples further illustrate the invention but, of course, should not be construed as in any way limiting its scope.

EXAMPLES

The materials and methods employed in Examples 1-13 are provided below.

Differentiation of hiPSC into TEPLC (Day 0-15)

Human induced pluripotent stem cells (hiPSC) (NL5-GFP) were maintained on ESSENTIAL 8 medium (Gibco, Waltham, MA). The medium was changed daily and cells were mechanically passaged into MATRIGEL matrix (BD Biosciences, Franklin Lakes, NJ) coated dishes at a 1:3 or 1:6 ratio every 2-3 days to expand and maintain the hiPSC before they begin to differentiate into thymic epithelial cells (prior to day 1). For differentiation of hiPSC into TEPLC, the protocol taught in Sun et al., *Cell Stem Cell*, 13: 230-236 (2013) was modified. In summary, hiPSCs were seeded into MATRIGEL matrix coated dishes with ESSENTIAL 8 medium+Rhok Inhibitor (FIG. 1, Days 0-1) to improve the survival of cells cultured in xeno-free conditions. The following differentiation step is as described in Sun et al. but differs by avoiding dissociation and adding a re-plating step on day 3 to allow hiPSC to form 3D structures and continue differentiation into thymic epithelial cells.

Stem Cell Culture and Differentiation

Figure 1:
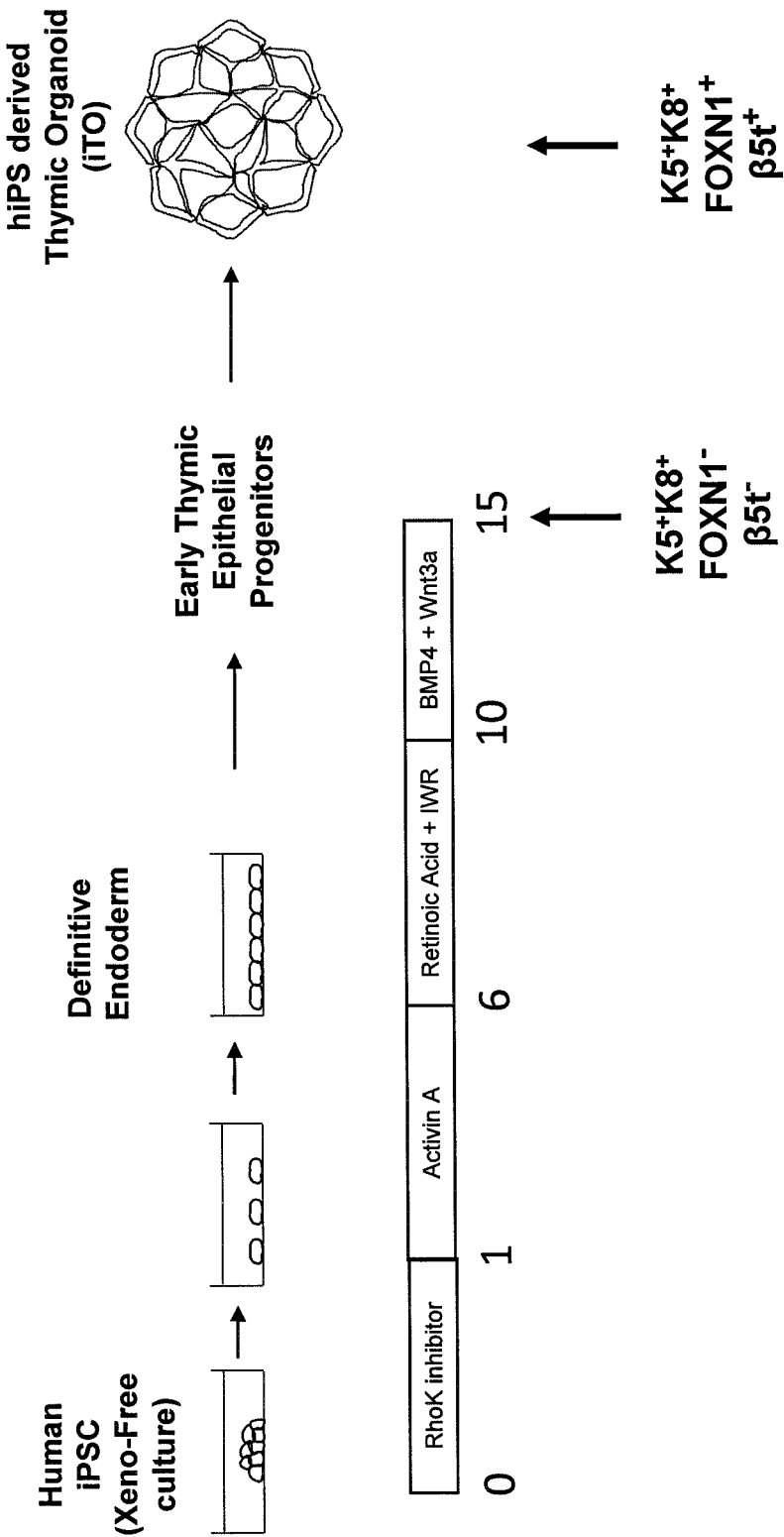
FIG. 1 is a schematic showing a method of producing a thymic organoid in vitro according to an embodiment of the invention.

Before induction, cells were washed briefly by phosphate buffer saline (PBS). hiPSCs were cultured in chemical-defined, serum-free X-VIVO 10 medium (Lonza, Basel, Switzerland) supplemented with 100 ng/ml ACTIVIN A protein (PeproTech, Rocky Hill, NJ) for 3 days. Cells were then dissociated with 0.25% trypsin and replated onto MATRIGEL-coated dishes at a density of 5000-10,000 cells/cm$^2$. Cells were cultured with the same differentiation medium for another two days (FIG. 1, Days 1-6). The differentiated cells were treated with 1 µM all-trans RA (Sigma, St. Louis, MO) and 2.5 µM IWR1 (Tocris, Bristol, UK) for 4 days (FIG. 1, Days 6-10). Then 10 ng/ml BMP4 and 50 ng/ml WNT3a (R&D Systems, Minneapolis, MN) were used for the induction of TEPCs (FIG. 1, Days 10-15). The X-VIVO 10 medium was used as a basal medium. All medium and additives were purchased from Invitrogen (Waltham, MA) unless otherwise noted.

Differentiation of TEPLC into K5+K8+FOXN1+3D Thymic Structures 3D thymic structures were mechanically picked up after 15 days of in vitro differentiation using micro surgical scissors under a phase contrast microscope. 2D cultures were cut off in squares of 3 mm×3 mm and cultured in suspension overnight in ultra-low attachment V bottom 96 well plates at 37° C. in TEC expansion media (MEBM (Lonza, Basel, Switzerland)+10% B27 (Gibco, Waltham, MA)+GLUTAMAX (X1) supplement (Thermo Fisher Scientific, Waltham, MA)+20 ng/ml hEGF+0.1 µM Cholera Toxin B+0.4 ng/ml Hydrocortisone+2.5 µg/ml Insulin). For organoid formation, 3D structures were picked up from multilayered differentiated hiPSC at day 15 with scissors and cultured in TEC expansion+100 ng/ml Wnt3a+100 ng/ml FGF7+50 ng/ml BMP4. For mesenchymal factor identification, the following reagents were added to previous media: 100 mg/ml FGF8, 100 ng/ml FGF10, 100 ng/ml IGF-1, KAAD-Cyclopamine 0.5 µM and TGFb RI Kinase inhibitor 5uM. In the case of MSC reaggregation, passage 3 human mesenchymal stem cells were seeded at 20,000 cells/organoid in a ultra-low attachment V bottom 96 well plate.

Confocal Microscopy of FTOCs

Primary Antibodies, Secondary Antibodies and IgG Isotypes were obtained from Abcam (Cambridge, UK). Formalin-fixed paraffin-embedded tissue sections were dewaxed by heating at 60° C. for 1 h followed by a 10-min xylene wash and then rehydrated in a decreasing ethanol series. After dewaxing, the slides were boiled for 15 min in 1× Antigen Retrieval CITRA PLUS buffer (catalog number HK086, BioGeneX, Fremont, CA) using a microwave. After an extensive wash in deionized water, the slides were immersed in 1× PBS. Before staining, both cell and tissue sections were blocked and permeabilized for 2 hours by PBS+1% PBS+0.1% TRITON X-100 surfactant (T-FBS) at 4° C. The primary Ab at 1:100 dilution in T-FBS buffer was incubated overnight at 4° C. After three washes with T-FBS, the samples were incubated with ALEXA FLUOR-conjugated secondary antibodies diluted at 1:200 in T-FBS buffer overnight at 4° C. followed by extensive wash with T-FBS. Before mounting, the nuclei were counterstained with DAPI (Vectorshield, Burlingame, CA). For whole organoid immunofluorescent staining, whole organoids were fixed overnight and blocked and permeabilized overnight by PBS+1% FBS+0.1% TritonX-100 (T-FBS) at 4° C. The primary Ab at 1:1000 dilution in T-FBS buffer was incubated overnight at 4° C. After three washes with T-FBS, the samples were incubated with Alexa Fluor-conjugated secondary antibodies diluted at 1:1000 in T-FBS buffer overnight at 4° C. followed by extensive wash with T-FBS. Before mounting, the nuclei were counterstained with DAPI (Vectorshield, Burlingame, CA). Fluorescence images were collected with a ZEISS LSM880 laser-scanning microscope (Carl Zeiss, Inc., Thornwood, NY) equipped with 20× Plan-apochromat (numerical aperture 0.8) objective lens.

Example 1

This example demonstrates the generation of early thymic epithelial progenitor like cells (TEPLC) from human iPSCs in xeno-free culture.

Two types of human iPSCs ((1) HCB:CD34+ human cord blood cell and (2) T-IPS: T cell-derived iPS) were cultured for one night in iPS ESSENTIAL 8 media (Thermo Fisher Scientific, Waltham, MA) and Rho kinase inhibitor to inhibit apoptosis and allow the cells to attach to the MATRIGEL plate coating overnight (FIG. 1, Days 0-1). The iPSCs were cultured in xeno-free media. As shown in FIG. 1, the cells were cultured in Activin A for 5 days (FIG. 1, Days 1-6). Retinoic acid and IWR, a Wnt signaling inhibitor, were added on day 6, and the cells were cultured for an additional 4 days (FIG. 1, Days 6-10). BMP4 and Wnt3a were added on day 10, and the cells were then cultured for an additional 5 days (FIG. 1, Days 10-15) for a total of 15 days in culture. By day 5, the cells had formed a definitive endoderm. Sections were picked up using micro surgical scissors on day 15 and subjected to fluorescence activated cell sorting (FACS). Control flow cytometry experiments measured detection of IgG(488) and IgG(APC) (FIGS. 2A and 2D). The hiPS derived early thymic epithelial progenitor-like cells identified by FACS on day 15 showed robust differentiation of K5$^+$/K8$^+$/FOXN1$^-$ TEPLCs from the different types of human iPS cells, as shown in FIGS. 2B-2C and 2E-2F.

Example 2

This example demonstrates that FOXN1 expression can be induced by extended culture of TEPLCs.

Human iPSCs were cultured as described in Example 1, but were not picked up on day 15. Instead, XF media was added to one culture while XF media plus 50 ng/ml of FGF7 and 50 ng/ml of Wnt3a were added to the second culture. On day 21 of the culture, sections of the cells formed in each culture were harvested and subjected to FACS. The results are shown in FIGS. 3A-3F. As shown in FIGS. 3A-3F, higher numbers of the Day 21 cells in both XF media only and XF+FGF7+Wnt3a media express FOXN1, as compared to the Day 15 cells. Microscopic analysis of the cells on day 21 revealed an astrocyte-like structure, similar to cells found in the human fetal thymic cortex.

Example 3

This example demonstrates the development of 3D spheroids from TEPLCs.

TEPLCs were differentiated from human iPSCs as described in Example 1 without dissociating the cells and without passaging the cells. By days 13-14 of culture, the cells started to from 3D spheroids in the center of overgrowth in the multilayered regions of the TEPLCs, as shown in FIG. 4.

Example 4

This example demonstrates the differentiation of 3D spheroids into thymic organoids and that the hiPS derived organoids formed 3-dimensional networks producing Keratin 5 and Keratin 8 at 42 days.

Human iPSCs were differentiated into 3-dimensional spheroids as described in Example 3. Squares of the cells growing in multilayers were cut out using micro surgical scissors and cultured in a 3D culture for 42 days in media designed for epithelial cell expansion: EBMB, B27 serum replacement, hydrocortisone, cholera toxin B, and human epidermal growth factor (EGF). On day 42, organoids were collected, measured, and stained with DAPI. The organoids formed were approximately 1 mm in diameter and were characterized by thin multilayers of cells that were K5$^+$/K8$^+$ (thymic epithelial cells). Staining also revealed that small regions of the organoid showed small layers of thymoproteosome β5t.

The method described in this Example contrasted with two dimensional (2D) culture methods, which are based on the premise that cells have to be symmetric on a flat surface. In 2D culture, when cells grow enough to cover all of a first culture surface, they are harvested and passaged to a lower density on a second culture surface.

Example 5

This example demonstrates that addition of certain media allowed continued ex-vivo growth of an iPS derived thymic organoid.

In order to determine which factors help maintain TEC expansion, diverse cytokines and growth factors were screened. Combinations of cytokines and growth factors tested include, among others, combinations of fibroblast growth factor 21 (FGF21), keratinocyte growth factor (KGF, also known as FGF7), Wnt3a, and BMP4. Small spheroids of thymic epithelial progenitor cells were grown as described in Example 3. On day 15, small K5$^+$/K8$^+$/FOXN1$^-$ spheroids, which formed in the multilayer dish, were mechanically picked up using micro surgical scissors under a phase contrast microscope and cultured under different variations of media compositions, including, for example, RPMI+L-Glutamine+10% FCS, aMEM+20% FCS+PS, MEBM+B27+Glutamax(1:100)+CTB(1:1000)+0.5 mg/ml HC(1:1000)+20 ng/ml hEGF(1:1000)+5 ug/ml Insulin(1:2000), EBMB+B27+Hidrocortisone+Cholera Toxin+hEGF, and MEBM+B27+0.5 mg/ml HC(1:1000)+20 ng/ml hEGF(1:1000)+5 ug/ml insulin(1:2000)+20 ng/ml hbFGF(1:500)+4 ng/ml heparin(1:500). It was found that addition of BMP4, Wnt3a, and FGF7 to the TEC media allows the spheroids to continue growing for 7 additional days, resulting in discrete iPS derived thymic organoids, as shown in FIGS. 5A-5B. Examination under microscope revealed an astrocyte-like structure. Staining with DAPI and GFP revealed expression of K5 and K8. IHC further revealed the expression of the FOXN1 transcription factor in the nucleus.

Example 6

This example demonstrates that spheroids surrounded by less differentiated thymic epithelial progenitors allow the spheroids to grow for longer growth periods. Spheroids were grown as described in Example 5. It was found that 3D culture of the spheroids that were grown for more than a week generated organoids that disintegrate, as shown in FIG. 6. It was hypothesized that the cells forming the spherical structures ("early TEPCs") are more differentiated than the lower levels of cells (TEPLCs), and the early TEPCs become exhausted from continuous expansion. It was further hypothesized that because the lower layer of cells is less differentiated, this layer can contribute to late stage organoid growth. To test these hypotheses, squares of the Day 14 thymic epithelial progenitor-like cells of the multilayer structure were cut with surgical scissors and 3D cultured in the TEC media plus BMP4, Wnt3a, and FGF7 for 42 days, as shown in FIG. 6. The squares included the more differentiated cells (A) and the less differentiated cells (B) of FIG. 6. On day 42, sections were cut, stained with DAPI, and subjected to immunohistochemistry. Staining of the resulting organoid revealed that the thymic organoids generate 3D structures of Keratin 5+/Keratin 8+cells. It was also revealed that some of the cut regions start to become K5 or K8 single positive cells. Without being bound to a particular theory or hypothesis, it is supposed that the TEPC will grow and differentiate into medullary and cortical TECs, which are the cells that mainly give function to the thymus. Cortical (single positive K8) and Medullary (single positive K5) usually develop into thymic tissue in later stages of development.

Example 7

This example demonstrates that the thymic organoids generate a K5+K8+ population similar to a human TEC progenitor region.

Thymic organoids were grown as described in Example 6, and sections were cut out on day 56. A section was stained and compared with a 16-week old human fetal thymus. The comparison revealed that most of the cells of the thymic organoid express Keratin 5 and Keratin 8 in amounts comparable to the human thymic epithelial cell progenitor stage cells (16 weeks). Staining also revealed that Day 56 sections of the thymic organoids also express thymoproteosome β5t, although in smaller amounts than in a human thymic cortex, suggesting that these cells may be thymic epithelial cells in transition from the progenitor stage. Staining further revealed the thymic organoid expressed DLL4 and IL-7 (a cytokine used in in vitro T cell generation).

Example 8

This example demonstrates that addition of mesenchymal stem cell (MSC) factors can produce thymic organoids with areas of β5t expressing cells.

It was hypothesized that because KGF (FGF7), BMP4, and Wnt3a contributed to growth of the organoid, as described in Example 5, and these factors are expressed by MSC, that additional MSC factors may facilitate development of the organoid. Therefore, one or more of the following additional factors were added to the media: FGF10, IGF-1, FGF8 (factors secreted by mesenchymal stem cells), and TGF inhibitor or cyclopamine (inhibitors or factors that impaired TEC expansion), as shown in Table 1. Sections were cut from organoids grown with these additional factors. Staining with DAPI revealed that the addition of one or more of these MSC factors and inhibitors reproducibly resulted in organoids with areas of β5t expressing cells, as shown in FIG. 7.

The following table presents data regarding the effect of certain MSC factors on hiTO generation.

TABLE 1

| | 1/5 Viable Organoids | 3/5 Viable Organoids | 7/7 Viable Organoids | 7/8 Viable Organoids |
|---|---|---|---|---|
| TEC Media | + | + | + | + |
| KGF7 | + | + | + | + |
| BMP4 | + | + | + | + |
| Wnt3a | + | + | + | + |
| FGF10 | − | + | + | + |
| IGF-1 | − | + | + | + |
| FGF8 | − | − | + | − |
| TGFβ$_{inh}$ | − | − | − | + |
| Cyclop | − | − | − | + |

Example 9

This example demonstrates that the addition of MSC factors improves the reproducibility of organoid formation.

To test whether the addition of human MSC factors would improve the reproducibility of the organoid formation, the experimental design shown in FIG. 8 was established. Thymic organoids that were produced as described in Example 5 and cultured in 3D for 42 days with the addition of MSCs. These organoids were not generated in a reproducible manner, indicating that MSCs may contain factors, in addition to the secreted human MSC factors listed in Example 8, that may limit organoid growth and survival. Therefore, TGFβ inhibitor (a factor which has been reported to decrease TEC survival) was used. After supplementary TGFΘ inhibitor was added, organoids were cut and stained at day 56. Day 56 thymic organoids were formed in a reproducible way, with a defined cortical region, and expressed thymoproteosome β5t with the same intensity as a 16 week old human fetal thymus. Thus, the addition of MSC factors plus TGFβ inhibitor facilitate the differentiation of TECs into a thymic organoid.

Example 10

This example demonstrates that the hiPSC-derived organoids express FOXN1.

The hiPSC-derived organoids were prepared and cultured in 3D culture for 7 days as described in Example 5. On day 7, images were taken via confocal microscopy which revealed that staining with DAPI showed the detection of the cell nuclei (FIG. 10A). The control IgG isotope was used as a negative control (not shown), and anti-FOXN1 antibodies conjugated with ALEXA FLUOR secondary antibodies were detected (FIG. 10B).

Example 11

This example demonstrates that hiTO cells express Keratin 5, Keratin 8, and thymoproteosome β5t.

The hiPSC-derived organoids were prepared and cultured in 3D culture for 42 days as described in Example 4. On day 42, images were taken via confocal microscopy. The images revealed the detection of nuclei stained with DAPI (FIG. 11A). The control IgG isotope was used as a negative control (not shown), and anti-Keratin-8 antibodies conjugated with ALEXA FLUOR secondary antibodies (FIG. 11B), anti-Keratin-5 antibodies conjugated with ALEXA FLUOR secondary antibodies (FIG. 12B), and thymoproteosome β5t conjugated with ALEXA FLUOR secondary antibodies (FIG. 13B) were all detected.

Example 12

This example demonstrates that hiTO cells express MHC class II cell surface receptor HLA-DR.

The hiPSC-derived organoids were prepared and cultured in 3D culture for 42 days as described in Example 4. On day 42, images were taken via confocal microscopy, which showed positive staining of antibodies specific for HLA-DR. The images revealed the detection of nuclei stained with DAPI (FIG. 14A). The control IgG isotope was detected only as background level (not shown), and anti-HLA-DR antibodies conjugated with ALEXA FLUOR secondary antibodies were detected (FIG. 14B).

Example 13

This example demonstrates that hiTO cells express DLL4 and IL-7,

The hiPSC-derived organoids were prepared and cultured in 3D culture for 42 days as described in Example 4. On day 42, images were taken via confocal microscopy, which showed the detection of nuclei stained with DAPI (FIGS. 15A and 16A), and the IgG control isotope was used as negative control (not shown). FIG. 15B shows the detection of anti-DLL4 antibodies conjugated with ALEXA FLUOR secondary antibodies. FIG. 16B shows the detection of anti-IL-7 antibodies conjugated with ALEXA FLUOR secondary antibodies.

Comparative Example 1

This comparative example demonstrates an attempt to produce a thymic organoid which failed.

A method of forming a thymic organoid was attempted. TECs were reaggregated by centrifugation, hydrogel, or suspension using combinations of human mesenchymal stem cells (hMSC), HUVEC (human umbilical endothelial cells) and human hematopoetic stem cells (HSC). The method failed to result in a thymic organoid.

Comparative Example 2

This comparative example demonstrates an attempt to produce a thymic organoid which failed.

Human fetal tissues were re-aggregated with iPS-derived TEPLCs. The method failed to result in a thymic organoid.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preparing a thymic organoid in vitro, the method comprising:
   (i) differentiating pluripotent stem cells into endodermal cells in vitro without enzymatically disassociating the pluripotent stem cells or the endodermal cells, wherein
(i) comprises replating the pluripotent stem cells on Day 3 of culture;

(ii) differentiating the endodermal cells into third pharyngeal pouch endodermal (PPE) cells in vitro without enzymatically dissociating the endodermal cells or the PPE cells;

(iii) differentiating the third PPE cells into thymic epithelial progenitor-like cells (TEPLCs) in an in vitro, two-dimensional culture without enzymatically dissociating the third PPE cells or the TEPLCs, wherein the TEPLCs are FOXN1 protein negative;

(iv) forming a three-dimensional spheroid by culturing the TEPLCs in an in vitro, three-dimensional culture and differentiating the TEPLCs into thymic epithelial progenitor cells (TEPCs) in an in vitro, three-dimensional culture without enzymatically dissociating the TEPLCs or the TEPCs, wherein the TEPCs are FOXN1 protein positive, wherein (iv) comprises differentiating the TEPLCs into TEPCs in the presence of one or more Mesenchymal Stem Cell (MSC) factors;

(v) differentiating the TEPCs into thymic epithelial cells (TECs) in the in vitro, three-dimensional culture in the presence of bone morphogenic protein 4 (BMP4); and (vi) forming the TECs into a thymic organoid in the in vitro, three-dimensional culture, wherein the thymic organoid expresses keratin 5, keratin 8, FOXN1 protein, β5t, delta like Notch ligand 4 (DLL4), and interleukin 7, and wherein the method does not comprise co-culturing the cells with mesenchyme or stromal cells.

2. The method according to claim 1, wherein (v) comprises differentiating the TEPCs into TECs in the in vitro, three-dimensional culture in the presence of one or both of Protein Wnt-3a (Wnt3a) and fibroblast growth factor 7 (FGF7).

3. The method of claim 1, wherein the method comprises culturing the pluripotent stem cells in mammalian cellular basement matrix for at least one day prior to (i).

4. The method of claim 1, wherein the TEPLCs are keratin $5^+$/keratin $8^+$.

5. The method of claim 1, wherein the method does not comprise passaging the cells.

6. The method of claim 1, wherein the thymic organoid comprises keratin $5^{high}$/keratin $8^{low}$ cells.

7. The method of claim 1, wherein the thymic organoid comprises keratin $5^{low}$/keratin $8^{high}$ cells.

8. The method of claim 1, wherein any one or more of (i)-(vi) is/are carried out in xeno-free medium.

9. The method of claim 1, further comprising culturing the thymic organoid to overexpress one or more autologous proteins which promote T cell differentiation.

10. The method of claim 9, wherein the one or more autologous proteins which promote T cell differentiation comprise one or more of DLL4 and IL-7.

11. The method of claim 1, wherein the one or more MSC factors comprise one or more of FGF7, BMP4, Wnt3a, fibroblast growth factor 10 (FGF10), insulin-like growth factor-1 (IGF-1), fibroblast growth factor 8 (FGF8), transforming growth factor β inhibitor (TGFβ$_{inh}$), and cyclopamine.

12. The method of claim 11, wherein the one or more of the MSC factors comprise FGF10, IGF-1, FGF8, TGFβ$_{inh}$, and cyclopamine.

13. A method of preparing thymic emigrant cells in vitro, the method comprising:
preparing a thymic organoid in vitro by the method of claim 1;
egressing the cells from the thymic organoid, wherein the cells egressing from the thymic organoid are thymic emigrant cells; and
isolating the thymic emigrant cells from the thymic organoid.

* * * * *